(12) United States Patent
Takahashi et al.

(10) Patent No.: US 8,304,554 B2
(45) Date of Patent: Nov. 6, 2012

(54) COMPOUND, COMPOSITION AND THIN FILM

(75) Inventors: Makoto Takahashi, Minami-ashigara (JP); Hideyuki Nishikawa, Minami-ashigara (JP); Ichiro Nagata, Minami-ashigara (JP); Satoshi Tanaka, Minami-ashigara (JP); Shigeki Uehira, Minami-ashigara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 184 days.

(21) Appl. No.: 12/659,022

(22) Filed: Feb. 23, 2010

(65) Prior Publication Data
US 2010/0222594 A1 Sep. 2, 2010

Related U.S. Application Data

(62) Division of application No. 11/660,039, filed as application No. PCT/JP2005/015102 on Aug. 12, 2005, now Pat. No. 7,696,353.

(30) Foreign Application Priority Data

Aug. 12, 2004 (JP) ................................. 2004-235350
Mar. 23, 2005 (JP) ................................. 2005-085016

(51) Int. Cl.
*C07D 413/14* (2006.01)
(52) U.S. Cl. ......................................................... 548/131
(58) Field of Classification Search ........................ None
See application file for complete search history.

(56) References Cited

U.S. PATENT DOCUMENTS

| | | | |
|---|---|---|---|
| 4,583,825 A | 4/1986 | Buzak | |
| 5,410,422 A | 4/1995 | Bos | |
| 5,518,783 A | 5/1996 | Kawata et al. | |
| 5,583,679 A | 12/1996 | Ito et al. | |
| 5,646,703 A | 7/1997 | Kamada et al. | |
| 5,774,197 A | 6/1998 | Nakamura | |
| 5,805,253 A | 9/1998 | Mori et al. | |
| 6,436,558 B1 | 8/2002 | Sato et al. | |
| 7,431,971 B2 | 10/2008 | Nishikawa et al. | |
| 7,431,972 B2 | 10/2008 | Nagai et al. | |
| 2002/0037427 A1 | 3/2002 | Taguchi | |
| 2005/0195348 A1 | 9/2005 | Saitoh et al. | |
| 2006/0114385 A1 | 6/2006 | Ito et al. | |
| 2006/0170851 A1 | 8/2006 | Kawamoto | |
| 2007/0091228 A1 | 4/2007 | Itadani et al. | |
| 2008/0090027 A1 | 4/2008 | Li et al. | |
| 2008/0113112 A1 | 5/2008 | Ikeda et al. | |
| 2008/0158483 A1 | 7/2008 | Saitoh et al. | |
| 2008/0193679 A1 | 8/2008 | Nishikawa et al. | |

FOREIGN PATENT DOCUMENTS

| | | |
|---|---|---|
| DE | 39 11 620 A1 | 10/1990 |
| DE | 102 34 188 A1 | 2/2004 |
| EP | 1 156 349 A1 | 11/2001 |
| EP | 1 506 991 A2 | 2/2005 |
| JP | 6-214116 A | 8/1994 |
| JP | 7-157473 A | 6/1995 |
| JP | 7-281028 A | 10/1995 |
| JP | 7-306317 A | 11/1995 |
| JP | 9-26572 A | 1/1997 |
| JP | 9-197397 A | 7/1997 |
| JP | 9-292522 A | 11/1997 |
| JP | 10-54982 A | 2/1998 |
| JP | 10-312166 A | 11/1998 |
| JP | 11-279165 A | 10/1999 |
| JP | 11-292848 A | 10/1999 |
| JP | 11-316378 A | 11/1999 |
| JP | 11-345686 A | 12/1999 |
| JP | 3056997 B2 | 6/2000 |
| JP | 2001-166147 A | 6/2001 |
| JP | 2002-20363 A | 1/2002 |
| JP | 2002-040429 A | 2/2002 |
| JP | 2003-57817 A | 2/2003 |
| JP | 2003-138251 A | 5/2003 |
| JP | 2004-184864 A | 7/2004 |
| JP | 2005-221962 A | 8/2005 |
| JP | 4431454 B2 | 12/2009 |
| KR | 10-2004-0055433 A | 6/2004 |
| WO | WO 96/37804 A1 | 11/1996 |

OTHER PUBLICATIONS

Kim et al. Tetrahedron Letters, (2001), vol. 42, p. 2697-2699.*
Office Action (Decision on Examination) issued by the Taiwanese Patent Office issued in corresponding Taiwanese Patent Application No. 094127418 dated Sep. 27, 2011, with an English translation thereof.
Cherioux F. et al., "Synthesis and electrochemical properties of new star-shaped thiophene oligomers and their polymers", Chemical Communications—Chemcom, Royal Society of Chemistry, GB, No. 20, 1998, pp. 2225-2226.

(Continued)

*Primary Examiner* — Yong Chu
(74) *Attorney, Agent, or Firm* — Buchanan Ingersoll & Rooney PC

(57) ABSTRACT

A compound represented by the following formula (DII):

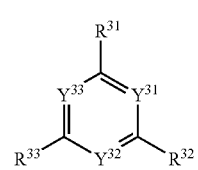

(DII)

wherein $Y^{31}$, $Y^{32}$ and $Y^{33}$ each independently represents a methine group or a nitrogen atom; $R^{31}$, $R^{32}$ and $R^{33}$ each independently represents the following formula (DII-R):

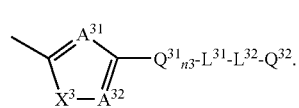

(DII-R)

9 Claims, No Drawings

OTHER PUBLICATIONS

J.B. Hynes et al., "Hydroxylamine Derivatives as Potential Antimalarial Agents, 3. 1,2,4-Oxadiazoles", Journal of Medicinal Chemistry, vol. 15, No. 11, 1972, pp. 1198-1200.
STN International document dated Jul. 10, 2009, issued on Jul. 15, 2009 in U.S. Appl. No. 11/660,039.
Kim et al., "Synthesis of Novel Discotic Mesogen Containing Electron-Transportable Oxadiazole Moiety", Molecular Crystals and Liquid Crystals, vol. 370, 2001, pp. 391-394, XP008055885.
Kim B G et al., "Star-shaped discotic nematic liquid crystal containing 1,3,5,-triethynylbenzene and oxadiazole-based rigid arms", Tetrahedron Letters, Elsevier, Amsterdam, Nl, vol. 42, No. 14, Apr. 2, 2001 pp. 2697-2699 XP004231644.
Cherioux F et al., "Synthesis and characterization of an octupolar polymer and new molecular octupoles with off-resonant third order optical nonlinearities", Chemical Communications—Chemcon, Royal society of Chemistry, GB, No. 20, 1999, pp. 2083-2084, XP002261155.
Cristiano R et al., "Synthesis and Characterization of Low Molecular Mass Luminescent Liquid Crystalline Materials With 1,3,4-Oxadiazole Units", Liquid Crystals, Taylor and Francis, Abingdon, GB, vol. 32, No. 1, Jan. 2005, pp. 7-14, XP001222748 ISSN: 0267-8292 abstract; compound II.
Cristiano R et al., "Light-Emitting Bent-Shape Liquid Crystals", Liquid Crystals, Taylor and Francis, Abingdon, GB, vol. 32, No. 1, Jan. 2005, pp. 15-25, XP001222749 ISSN: 0267-8292, abstract; figure 1.
Office Action (Notification for the Opinion of Examination) issued by the Taiwanese Patent Office issued in corresponding Taiwanese Patent Application No. 094127418 dated May 18, 2011, with an English translation thereof.
Japanese Office Action issued on Jun. 8, 2010 in Japanese Patent Application No. 2005-085016, with English translation thereof.

* cited by examiner

COMPOUND, COMPOSITION AND THIN FILM

CROSS-REFERENCE TO RELATED APPLICATIONS

This application is a divisional of application Ser. No. 11/660,039 filed Feb. 12, 2007, the contents of which are incorporated herein by reference, which was the National Stage filing under 35 U.S.C. §371 of International Application No. PCT/2005/015102 filed Aug. 12, 2005 (published in English as WO 2006/016724 A2, on Feb. 16, 2006), which in turn claims priority to Japanese Application Nos. 2004-235350 filed Aug. 12, 2004, and 2005-085016 filed Mar. 23, 2005.

TECHNICAL FIELD

The present invention relates to a compound having a benzene skeleton with 5-membered heterocyclic groups in the side branches thereof, to a composition and to a thin film. In particular, the invention relates to a liquid-crystalline compound favorable for fabrication of retarders, and to its use.

BACKGROUND ART

Heretofore, it is know that discotic liquid-crystalline compounds are extremely important compounds for a material for optically-compensatory films, for example, a described in JP-A-8-50206. As a liquid-crystalline compound that expresses discotic liquid-crystallinity, disclosed is 2,3,6,7,10,11-hexa{4-(4-acryloyloxyhexyloxy) benzoyloxy}triphenylene (JP-A-7-306317). The liquid-crystalline compound is used in many optically-compensatory sheets heretofore know in the art.

On the other hand, the wavelength dispersiveness of optically-compensatory sheets must be controlled in accordance with the liquid-crystal display devices, as disclosed in JP-A-2004-184864. However, nothing has heretofore been reported, relating to liquid-crystalline compounds of which the wavelength dispersiveness is smaller than that of 2,3,6,7,10,11-hexa{4-(4-acryloyloxyhexyloxy) benzoyloxy}triphenylene (that is, those having a smaller value of Re (at short wavelength (e.g., 450 nm)/Re (at long wavelength (e.g., 650 nm)).

The retardation (Δnd) of optically-compensatory sheets must be determined depending on the optical properties of the liquid-crystal cells to be compensated by the sheet. The retardation (Δnd) as referred to herein is a product of the refractivity anisotropy (Δn) of an optically-anisotropic layer and the thickness (d) of the optically-anisotropic layer. When the refractivity anisotropy (Δn) of an optically-anisotropic layer is large, then the liquid-crystal cell could be compensated even though the thickness (d) of the layer is thin. On the contrary, when the refractivity anisotropy (Δn) of an optically-anisotropic layer is small, then the thickness (d) of the layer must be large, and, as a result, there may often occur a defective problem in point of the alignment of liquid-crystalline compounds.

As a discotic liquid-crystalline compound having a large refractivity anisotropy (Δn) known is 2,3,6,7,10,11-hexa{4-(4-acryloyloxyhexyloxy)cinnamoyloxy}triphenylene as disclosed in JP-A-2001-166147. However, it has become obvious that the wavelength dispersiveness of this liquid-crystalline compound is larger than that of 2,3,6,7,10,11-hexa{4-(4-acryloyloxyhexyloxy)benzoyloxy}triphenylene.

Heterocyclic group-having tri-substituted benzenes are reported in *Molecular Crystals and Liquid Crystals*, 2001, Vol. 370, page 391. As a result of our studies, however, we, the present inventors have found that the compounds having that skeleton could not readily attain a lower wavelength dispersion than that of 2,3,6,7,10,11-hexa{4-alkyloxybenzoyloxy}triphenylene as so described in the Examples given hereinunder.

In consideration of the situation as above, an object of the invention is to provide a compound having a low wavelength dispersiveness that could not be realized by any conventional discotic liquid-crystalline compounds. Another object of the invention is to provide a liquid-crystalline compound capable of satisfying both low wavelength dispersiveness and high Δn. Still another object of the invention is to provide a composition containing the compound, and to provide a thin film formed by the use of the compound.

SUMMARY OF THE INVENTION

The above-mentioned objects can be attained by the invention mentioned below.

(1) A compound represented by the following formula (DI):

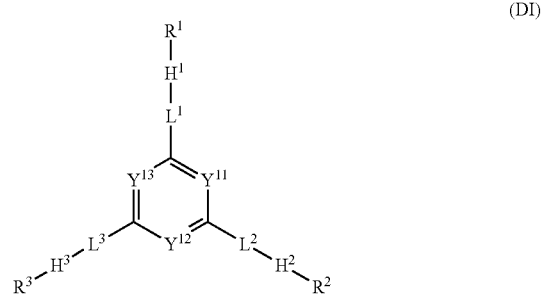

wherein $Y^{11}$, $Y^{12}$ and $Y^{13}$ each independently represent a methine group or a nitrogen atom; $L^1$, $L^2$ and $L^3$ each independently represent a single bond or a divalent linking group; $H^1$, $H^2$ and $H^3$ each independently represent a group represented by the following formula (DI-A) or (DI-B); $R^1$, $R^2$ and $R^3$ each independently represent a group represented by the following formula (DI-R):

wherein $YA^1$ and $YA^2$ each independently represent a methine group or a nitrogen atom; XA represents an oxygen atom, a sulfur atom, a methylene group or an imino group; * indicates the position at which the group of formula (DI-A) bonds to any of $L^1$ to $L^3$ in formula (DI); ** indicates the position at which the group of formula (DI-A) bonds to any of $R^1$ to $R^3$ in formula (DI),

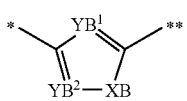

(DI-B)

wherein $YB^1$ and $YB^2$ each independently represent a methine group or a nitrogen atom; XB represents an oxygen atom, a sulfur atom, a methylene group or an imino group; * indicates the position at which the group of formula (DI-B) bonds to any of $L^1$ to $L^3$ in formula (DI); ** indicates the position at which the group of formula (DI-B) bonds to any of $R^1$ to $R^3$ in formula (DI),

(DI-R)

wherein * indicates the position at which the group of formula (DI-R) bonds to any of $H^1$ to $H^3$ in formula (DI); $L^{21}$ represents a single bond or a divalent linking group; $Q^2$ represents a divalent group having at least one cyclic structure; n1 indicates an integer of from 0 to 4; $L^{22}$ represents —O—, —O—CO—, —CO—O—, —O—CO—O—, —S—, —NH—, —SO$_2$—, —CH$_2$—, —CH=CH— or —C≡C—; ** indicates the position at which the group bonds to $Q^2$; $L^{23}$ represents a divalent linking group selected from —O—, —S—, —C(=O)—, —SO$_2$—, —NH—, —CH$_2$—, —CH=CH— and —C≡C— and their combinations, and when the divalent linking group contains a hydrogen atom, then the hydrogen atom may be substituted with a substituent; $Q^1$ represents a polymerizable group or a hydrogen atom, and when the polymerizable group contains a hydrogen atom, then the hydrogen atom may be substituted with a substituent; when n1 is 2 or more, then plural (-$L^{21}$-$Q^2$)'s may be the same or different.

(2) A compound represented by the following formula (DII), in particular, a liquid-crystalline compound represented by the following formula (DII):

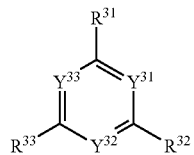

(DII)

wherein $Y^{31}$, $Y^{32}$ and $Y^{33}$ each independently represent a methine group or a nitrogen atom; $R^{31}$, $R^{32}$ and $R^{33}$ each independently represents the following formula (DII-R):

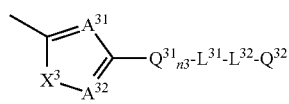

(DII-R)

wherein $A^{31}$ and $A^{32}$ each independently represent a methine group or a nitrogen atom; $X^3$ represents an oxygen atom, a sulfur atom, a methylene group or an imino group; $Q^{31}$ represents a 6-membered cyclic structure-having divalent linking group; n3 indicates an integer of from 1 to 3; $L^{31}$ represents *—O—, *—O—CO—, *—CO—O—, *—O—CO—O—, *—S—, *—NH—, *—SO$_2$—, *—CH$_2$—, *—CH=CH— or *—C≡C—; * indicates the position at which the group bonds to $Q^{31}$; $L^{32}$ represents a divalent linking group selected from —O—, —S—, —C(=O)—, —SO$_2$—, —NH—, —CH$_2$—, —CH=CH— and —C≡C— and their combinations, and when the divalent linking group contains a hydrogen atom, then the hydrogen atom may be substituted with a substituent; $Q^{32}$ represents a polymerizable group or a hydrogen atom, and when the polymerizable group contains a hydrogen atom, then the hydrogen atom may be substituted with a substituent; when n3 is 2 or more, then plural $Q^{31}$'s may be the same or different.

(3) A composition containing the liquid-crystalline compound of (1) and/or (2).

(4) A thin film where the liquid-crystalline compounds of (1) and/or (2) are uniformly aligned.

(5) A thin film of (4) where the alignment is fixed.

According to the invention, it has become possible to provide a compound (preferably a liquid-crystalline compound) satisfying both high Δn and low wavelength dispersiveness that could not be realized by conventional discotic liquid-crystalline compounds. In addition, it has also become possible to provide a composition (preferably a liquid-crystal composition) and a thin film comprising the compound.

BEST MODE FOR CARRYING OUT THE INVENTION

The invention is described in detail hereinunder. In this description, the numerical range expressed by the wording "a number to another number" means the range that falls between the former number indicating the lowermost limit of the range and the latter number indicating the uppermost limit thereof.

The compound of the invention is represented by the following formula (DI):

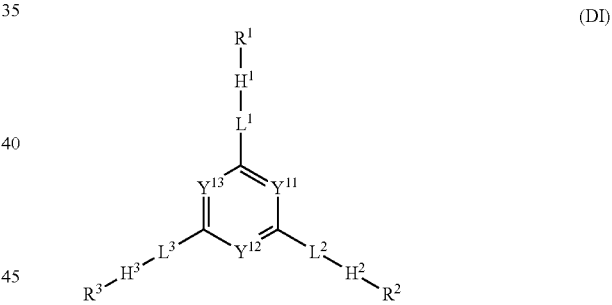

(DI)

In formula (DI), $Y^{11}$, $Y^{12}$ and $Y^{13}$ each independently represent a methine group or a nitrogen atom.

When $Y^{11}$, $Y^{12}$ and $Y^{13}$ are a methine group, then the hydrogen atom of the methine (CH) may be substituted with a substituent. Preferred examples of the substituent that the methine may have are an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom (preferably, fluorine atom, chlorine atom) and a cyano group. Of those substituents, more preferred are an alkyl group, an alkoxy group, an alkoxycarbonyl group, an acyloxy group, a halogen atom and a cyano group; and most preferred are an alkyl group having from 1 to 12 carbon atoms, an alkoxy group having from 1 to 12 carbon atoms, an alkoxycarbonyl group having from 2 to 12 carbon atoms, an acyloxy group having from 2 to 12 carbon atoms, a halogen atom and a cyano group.

More preferably, $Y^{11}$, $Y^{12}$ and $Y^{13}$ are all methine groups; and most preferably, the methine for them is unsubstituted.

In formula (DI), $L^1$, $L^2$ and $L^3$ each independently represent a single bond or a divalent linking group. When $L^1$, $L^2$ and $L^3$ are a divalent linking group, then it is preferably a divalent linking group selected from —O—, —S—, —C(=O)—, —NR$^7$—, —CH=CH—, —C≡C—, a divalent cyclic group and their combinations. $R^7$ represents an alkyl group having from 1 to 7 carbon atoms, or a hydrogen atom, preferably an alkyl group having from 1 to 4 carbon atoms, or a hydrogen atom, more preferably a methyl group, an ethyl group or a hydrogen atom, most preferably a hydrogen atom.

The divalent cyclic group for $L^1$, $L^2$ and $L^3$ is a divalent linking group having at least one cyclic structure (hereinafter this may be referred to as a cyclic group). The cyclic group is preferably 5-membered, 6-membered or 7-membered, more preferably 5-membered or 6-membered, most preferably 6-membered. The ring in the cyclic group may be a condensed ring. However, the ring is more preferably a single ring than a condensed ring. The ring in the cyclic group may be any of aromatic ring, aliphatic ring or heterocyclic ring. Preferred examples of the aromatic ring are benzene ring and naphthalene ring. A preferred example of the aliphatic ring is cyclohexane ring. Preferred examples of the hetero ring are pyridine ring and pyrimidine ring. More preferably, the cyclic group is an aromatic ring or hetero ring. The divalent cyclic group in the invention is more preferably a divalent linking group of a cyclic structure alone (which, however, may have a substituent), and the same shall apply hereinunder.

Of the divalent cyclic group represented by $L^1$, $L^2$ and $L^3$, the cyclic group having a benzene ring is preferably a 1,4-phenylene group. The cyclic group having a naphthalene ring is preferably a naphthalene-1,5-diyl group and a naphthalene-2,6-diyl group. The cyclic group having a cyclohexane ring is preferably a 1,4-cyclohexylene group. The cyclic group having a pyridine ring is preferably a pyridine-2,5-diyl group. The cyclic group having a pyrimidine ring is preferably a pyrimidine-2,5-diyl group.

The divalent cyclic group represented by $L^1$, $L^2$ and $L^3$ may have a substituent. The substituent includes a halogen atom (preferably, fluorine atom, chlorine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms.

Preferably, $L^1$, $L^2$ and $L^3$ are a single bond, *—O—CO—, *—CO—O—, *—CH=CH—, *—C≡C—, *-divalent cyclic group-, *—O—CO-divalent cyclic group-, *—CO—O-divalent cyclic group-, *—CH=CH-divalent cyclic group-, *—C≡C-divalent cyclic group-, *-divalent cyclic group-O—CO—, *-divalent cyclic group-CO—O—, *-divalent cyclic group-CH=CH— or *-divalent cyclic group-C≡C—; more preferably, a single bond, *—CH=CH—, *—C≡C—, *—CH=CH-divalent cyclic group- or *—C≡C-divalent cyclic group; most preferably a single bond. In these, * indicates the position at which the group bonds to the 6-membered ring that contains $Y^{11}$, $Y^{12}$ and $Y^{13}$ in formula (DI).

$H^1$, $H^2$ and $H^3$ each independently represent the following formula (DI-A) or (DI-B):

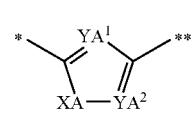

(DI-A)

In formula (DI-A), $YA^1$ and $YA^2$ each independently represent a methine group or a nitrogen atom. Preferably, at least one of $YA^1$ and $YA^2$ is a nitrogen atom; more preferably both are nitrogen atoms. XA represents an oxygen atom, a sulfur atom, a methylene group or an imino group, preferably an oxygen atom. * indicates the position at which the group bonds to any of $L^1$ to $L^3$ in formula (DI); ** indicates the position at which the group bonds to any of $R^1$ to $R^3$ in formula (DI)).

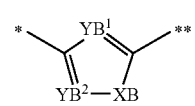

(DI-B)

In formula (DI-B), $YB^1$ and $YB^2$ each independently represent a methine group or a nitrogen atom. Preferably, at least one of $YB^1$ and $YB^2$ is a nitrogen atom; more preferably both are nitrogen atoms. XB represents an oxygen atom, a sulfur atom, a methylene group or an imino group, preferably an oxygen atom. * indicates the position at which the group bonds to any of $L^1$ to $L^3$ in formula (DI); ** indicates the position at which the group bonds to any of $R^1$ to $R^3$ in formula (DI)).

$R^1$, $R^2$ and $R^3$ each independently represent the following formula (DI-R):

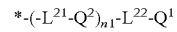

*-(-L$^{21}$-Q$^2$)$_{n1}$-L$^{22}$-Q$^1$      (DI-R)

In formula (DI-R), * indicates the position at which the group bonds to any of $H^1$ to $H^3$ in formula (DI).

$L^{23}$ represents a single bond or a divalent linking group. When $L^{21}$ is a divalent linking group, it is preferably a divalent linking group selected from —O—, —S—, —C(=O)—, —NR$^7$—, —CH=CH— and —C≡C— and their combinations. $R^7$ represents an alkyl group having from 1 to 7 carbon atoms, or a hydrogen atom, preferably an alkyl group having from 1 to 4 carbon atoms, or a hydrogen atom, more preferably a methyl group, an ethyl group or a hydrogen atom, most preferably a hydrogen atom.

Preferably, $L^{21}$ is any of a single bond, *—O—CO—, *—CO—O—, *—CH=CH— or *—C≡C— (in which *** indicates the position at which the group bonds to the side of * in formula (DI-R)), more preferably a single bond.

$Q^2$ represents a divalent group having at least one cyclic structure (cyclic group). The cyclic group is preferably a 5-membered, 6-membered or 7-membered cyclic group, more preferably a 5-membered or 6-membered cyclic group, most preferably a 6-membered cyclic group. The cyclic structure in the cyclic group may be a condensed ring. However, it is more preferably a single ring than a condensed ring. The ring in the cyclic group may be any of aromatic ring, aliphatic ring or heterocyclic ring. Preferred examples of the aromatic ring are benzene ring, naphthalene ring, anthracene ring and phenanthrene ring. A preferred example of the aliphatic ring is cyclohexane ring. Preferred examples of the hetero ring are pyridine ring and pyrimidine ring.

For $Q^2$, the cyclic group having a benzene ring is preferably a 1,4-phenylene group. The cyclic group having a naphthalene ring is preferably a naphthalene-1,4-diyl group, a naphthalene-1,5-diyl group, a naphthalene-1,6-diyl group, a naphthalene-2,5-diyl group, a naphthalene-2,6-diyl group and a naphthalene-2,7-diyl group. The cyclic group having a cyclohexane ring is preferably a 1,4-cyclohexylene group. The cyclic group having a pyridine ring is preferably a pyridine-2,5-diyl group. The cyclic group having a pyrimidine ring is preferably a pyrimidine-2,5-diyl group. Of those, especially preferred are a 1,4-phenylene group, a naphthalene-2,6-diyl group and a 1,4-cyclohexylene group.

$Q^2$ may have a substituent. Examples of the substituent are a halogen atom (preferably, fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; even more preferred are a halogen atom, an alkyl group having from 1 to 3 carbon atoms, and a trifluoromethyl group.

n1 indicates an integer of from 0 to 4, preferably an integer of from 1 to 3, more preferably 1 or 2.

$L^{22}$ represents —O—, —O—CO—, —CO—O—, —O—CO—O—, —S—, —NH—, —SO$_2$—, —CH$_2$—, —CH═CH— or —C≡C—; ** indicates the position at which the group bonds to $Q^2$.

Preferably, $L^{22}$ is —O—, —O—CO—, —CO—O—, —O—CO—O—, —CH$_2$—, —CH═CH— or —C≡C—; more preferably —O—, —O—CO—, —O—CO—O— or **—CH$_2$—. When $L^{22}$ is a group containing a hydrogen atom, then the hydrogen atom may be substituted with a substituent. Preferred examples of the substituent are a halogen atom, a cyano group, a nitro group, an alkyl group having from 1 to 6 carbon atoms, a halogen-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl-substituted carbamoyl group having from 2 to 6 carbon atoms, and an acylamino group having from 2 to 6 carbon atoms; and more preferred are a halogen atom, and an alkyl group having from 1 to 6 carbon atoms.

$L^{23}$ represents a divalent linking group selected from —O—, —S—, —C(═O)—, —SO$_2$—, —NH—, —CH$_2$—, —CH═CH— and —C≡C— and their combinations. The hydrogen atom in —NH—, —CH$_2$— and —CH═CH— may be substituted with a substituent. Preferred examples of the substituent are a halogen atom, a cyano group, a nitro group, an alkyl group having from 1 to 6 carbon atoms, a halogen-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl-substituted carbamoyl group having from 2 to 6 carbon atoms, and an acylamino group having from 2 to 6 carbon atoms; and more preferred are a halogen atom, and an alkyl group having from 1 to 6 carbon atoms. Substituted with any of these substituents, the liquid-crystalline compound of the invention may have an increased solubility in solvents used in preparing liquid-crystalline compositions containing the compound.

Preferably, $L^{23}$ is selected from a group consisting of —O—, —C(═O)—, —CH$_2$—, —CH═CH— and —C≡C— and their combinations. More preferably, $L^{23}$ contains from 1 to 20 carbon atoms, even more preferably from 2 to 14 carbon atoms. Also preferably, $L^{23}$ contains from 1 to 16 (—CH$_2$—)s, more preferably from 1 to 12 (—CH$_2$—)s.

$Q^1$ represents a polymerizable group or a hydrogen atom. When the liquid-crystalline compound of the invention is used in optical films such as optically-compensatory films of which the retardation is desired to be unchangeable by heat, then $Q^1$ is preferably a polymerizable group. Preferably, the polymerization for the group is addition polymerization (including ring-cleavage polymerization) or condensation polymerization. Specifically, it is desirable that the polymerizable group is a functional group that may undergo addition polymerization or condensation polymerization. Examples of the polymerizable group are mentioned below.

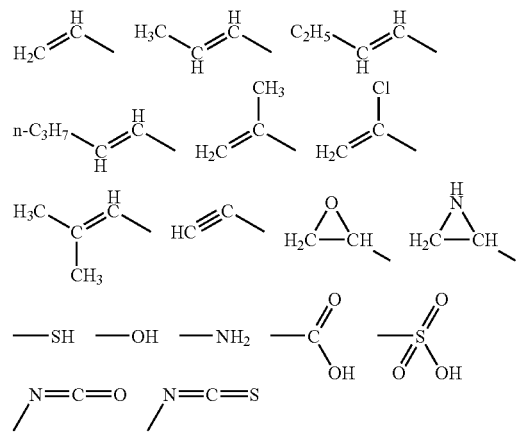

More preferably, the polymerizable group is a functional group that may undergo addition polymerization. As the polymerizable group of the type, preferred is a polymerizable ethylenic unsaturated group or a ring-cleavage polymerizable group.

Examples of the polymerizable ethylenic unsaturated group are the following formulae (M-1) to (M-6):

(M-1)

(M-2)

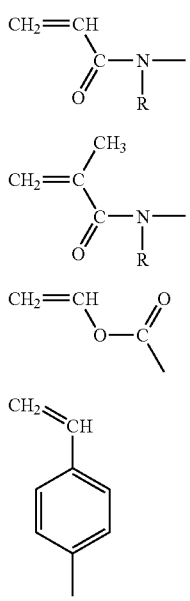

In formulae (M-3) and (M-4), R represents a hydrogen atom or an alkyl group, preferably a hydrogen atom or a methyl group.

Of formulae (M-1) to (M-6), preferred is formula (M-1) or (M-2), and more preferred is formula (M-1).

The ring-cleavage polymerizable group is preferably a cyclic ether group, more preferably an epoxy group or an oxetanyl group, and most preferably an epoxy group.

As the compounds of the invention, preferred are those of the following formula (DII):

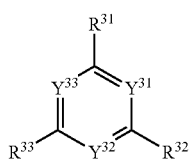

In formula (DII), $Y^{31}$, $Y^{32}$ and $Y^{33}$ each independently represent a methine group or a nitrogen atom, and these have the same meanings as $Y^{11}$, $Y^{12}$ and $Y^{13}$ in formula (DI). Their preferred ranges are also the same as therein.

In formula (DII), $R^{31}$, $R^{32}$ and $R^{33}$ each independently represents the following formula (DII-R):

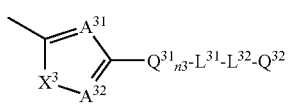

In formula (DII-R), $A^{31}$ and $A^{32}$ each independently represent a methine group or a nitrogen atom. Preferably, at least one of them is a nitrogen atom, more preferably both are nitrogen atoms. $X^3$ represents an oxygen atom, a sulfur atom, a methylene group or an imino group, preferably an oxygen atom.

$Q^{31}$ represents a 6-membered cyclic structure-having divalent linking group (this may be hereinafter referred to as a 6-membered cyclic group). The 6-membered ring may be a condensed ring. However, the ring is more preferably a single ring than a condensed ring. The ring in the 6-membered cyclic group may be any of aromatic ring, aliphatic ring or heterocyclic ring. Preferred examples of the aromatic ring are benzene ring, naphthalene ring, anthracene ring and phenanthrene ring. A preferred example of the aliphatic ring is cyclohexane ring. Preferred examples of the hetero ring are pyridine ring and pyrimidine ring.

For $Q^{31}$, the 6-membered cyclic group having a benzene ring is preferably a 1,4-phenylene group. The cyclic structure having a naphthalene ring is preferably a naphthalene-1,4-diyl group, a naphthalene-1,5-diyl group, a naphthalene-1,6-diyl group, a naphthalene-2,5-diyl group, a naphthalene-2,6-diyl group and a naphthalene-2,7-diyl group. The cyclic structure having a cyclohexane ring is preferably a 1,4-cyclohexylene group. The cyclic structure having a pyridine ring is preferably a pyridine-2,5-diyl group. The cyclic structure having a pyrimidine ring is preferably a pyrimidine-2,5-diyl group. Of those, especially preferred are a 1,4-phenylene group, a naphthalene-2,6-diyl group and a 1,4-cyclohexylene group.

The cyclic structure for $Q^{31}$ may have a substituent. Examples of the substituent are a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl group-substituted carbamoyl group having from 2 to 16 carbon atoms, and an acylamino group having from 2 to 16 carbon atoms. As the substituent for the 6-membered cyclic group, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; even more preferred are a halogen atom, an alkyl group having from 1 to 3 carbon atoms, and a trifluoromethyl group.

n3 indicates an integer of from 1 to 3, preferably 1 or 2.

$L^{31}$ represents *—O—, *—O—CO—, *—CO—O—, *—O—CO—O—, *—S—, *—N(R)—, *—CH$_2$—, *—CH═CH— or *—C≡C—; * indicates the position at which the group bonds to $Q^{31}$. Concretely, this has the same meaning as $L^{22}$ in formula (DI-R), and its preferred range is also the same as therein.

$L^{32}$ represents a divalent linking group selected from —O—, —S—, —C(═O)—, —NH—, —CH$_2$—, —CH═CH— and —C≡C— and their combinations. Concretely, this has the same meaning as $L^{23}$ in formula (DI-R), and its preferred range is also the same as therein.

In formula (DII-R), $Q^{32}$ has the same meaning as $Q^1$ in formula (DI-R).

Specific examples of the compounds of formula (DI) are mentioned below, to which, however, the invention should not be limited.

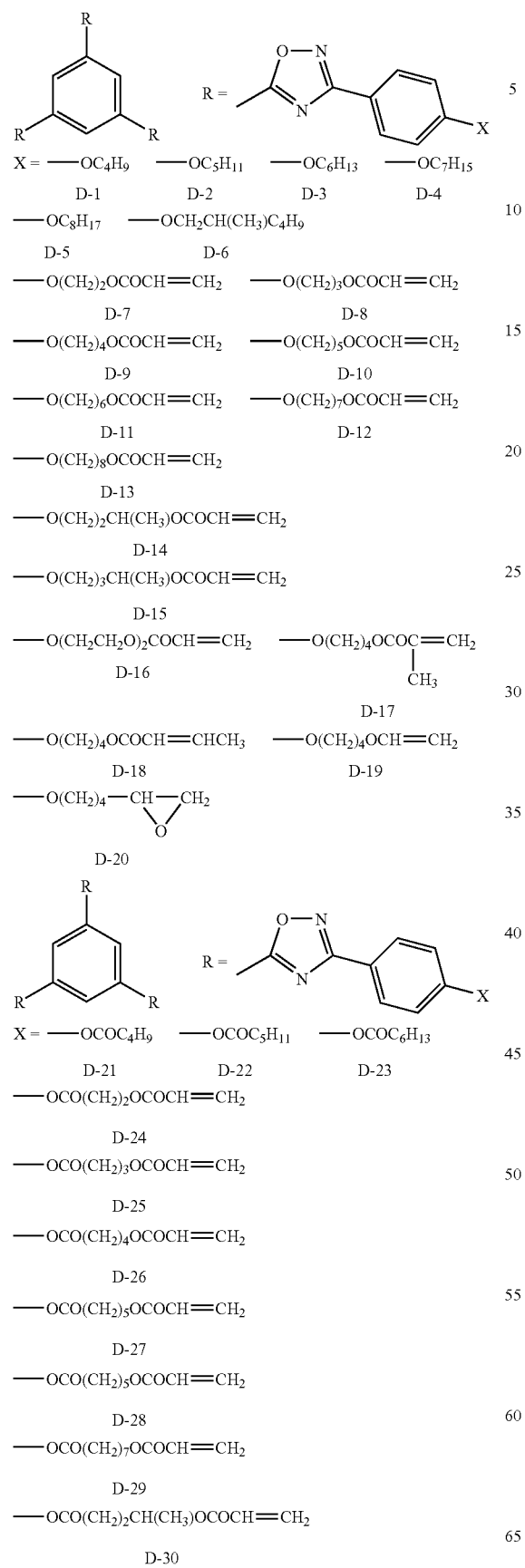

X = —OC₄H₉ —OC₅H₁₁ —OC₆H₁₃ —OC₇H₁₅
D-1      D-2       D-3       D-4
—OC₈H₁₇  —OCH₂CH(CH₃)C₄H₉
D-5      D-6
—O(CH₂)₂OCOCH=CH₂   —O(CH₂)₃OCOCH=CH₂
D-7                  D-8
—O(CH₂)₄OCOCH=CH₂   —O(CH₂)₅OCOCH=CH₂
D-9                  D-10
—O(CH₂)₆OCOCH=CH₂   —O(CH₂)₇OCOCH=CH₂
D-11                 D-12
—O(CH₂)₈OCOCH=CH₂
D-13
—O(CH₂)₂CH(CH₃)OCOCH=CH₂
D-14
—O(CH₂)₃CH(CH₃)OCOCH=CH₂
D-15
—O(CH₂CH₂O)₂COCH=CH₂   —O(CH₂)₄OCOC(CH₃)=CH₂
D-16                    D-17
—O(CH₂)₄OCOCH=CHCH₃   —O(CH₂)₄OCH=CH₂
D-18                   D-19
—O(CH₂)₄—CH—CH₂
         \O/
D-20

X = —OCOC₄H₉  —OCOC₅H₁₁  —OCOC₆H₁₃
D-21         D-22         D-23
—OCO(CH₂)₂OCOCH=CH₂
D-24
—OCO(CH₂)₃OCOCH=CH₂
D-25
—OCO(CH₂)₄OCOCH=CH₂
D-26
—OCO(CH₂)₅OCOCH=CH₂
D-27
—OCO(CH₂)₆OCOCH=CH₂
D-28
—OCO(CH₂)₇OCOCH=CH₂
D-29
—OCO(CH₂)₂CH(CH₃)OCOCH=CH₂
D-30

—OCO(CH₂)₂OCOC(CH₃)=CH₂
D-31
—OCO(CH₂)₂OCOCH=CHCH₃
D-32
—OCO(CH₂)₄OCH=CH₂   —OCO(CH₂)₄—CH—CH₂
D-33                              \O/
                     D-34

X = —OCOOC₄H₉  —OCOOC₅H₁₁  —OCOOC₆H₁₃
D-35           D-36          D-37
—OCOO(CH₂)₂OCOCH=CH₂
D-38
—OCOO(CH₂)₃OCOCH=CH₂
D-39
—OCOO(CH₂)₄OCOCH=CH₂
D-40
—OCOO(CH₂)₅OCOCH=CH₂
D-41
—OCOO(CH₂)₆OCOCH=CH₂
D-42
—OCOO(CH₂)₇OCOCH=CH₂
D-43
—OCOOCH(CH₃)CH₂CH₂OCOCH=CH₂
D-44
—OCOOC(CH₂CH₂O)₂COCH=CH₂
D-45
—OCOO(CH₂)₂OCOC=CH₂
              |
              CH₃
D-46
—OCOO(CH₂)₂OCOCH=CHCH₃
D-47
—OCOO(CH₂)₄OCH=CH₂
D-48
—OCOO(CH₂)₄—CH—CH₂
            \O/
D-49

X = —OC₄H₉ —OC₅H₁₁ —OC₆H₁₃ —OC₇H₁₅
D-50    D-51      D-52      D-53

—OC₈H₁₇    —OCH₂CH(CH₃)C₄H₉
  D-54         D-55
—O(CH₂)₂OCOCH=CH₂    —O(CH₂)₃OCOCH=CH₂
  D-56                  D-57
—O(CH₂)₄OCOCH=CH₂    —O(CH₂)₅OCOCH=CH₂
  D-58                  D-59
—O(CH₂)₆OCOCH=CH₂    —O(CH₂)₇OCOCH=CH₂
  D-60                  D-61
—O(CH₂)₈OCOCH=CH₂
  D-62
—O(CH₂)₂CH(CH₃)OCOCH=CH₂
  D-63
—O(CH₂)₃CH(CH₃)OCOCH=CH₂
  D-64
—O(CH₂CH₂O)₂COCH=CH₂    —O(CH₂)₄OCOC(CH₃)=CH₂
  D-65                         D-66
—O(CH₂)₄OCOCH=CHCH₃    —O(CH₂)₄OCH=CH₂
  D-67                      D-68
—O(CH₂)₄—CH—CH₂
           \\O/
  D-69

[Structure: 1,3,5-trisubstituted benzene with R groups; R = 5-methyl-3-(2-fluoro-4-X-phenyl)-1,2,4-oxadiazole]

X =  —OCOC₄H₉    —OCOC₅H₁₁    —OCOC₆H₁₃
      D-70          D-71          D-72
—OCO(CH₂)₂OCOCH=CH₂
  D-73
—OCO(CH₂)₃OCOCH=CH₂
  D-74
—OCO(CH₂)₄OCOCH=CH₂
  D-75
—OCO(CH₂)₅OCOCH=CH₂
  D-76
—OCO(CH₂)₆OCOCH=CH₂
  D-77
—OCO(CH₂)₇OCOCH=CH₂
  D-78
—OCO(CH₂)₂CH(CH₃)OCOCH=CH₂
  D-79
—OCO(CH₂)₂COC(CH₃)=CH₂
  D-80
—OCO(CH₂)₂OCOCH=CHCH₃
  D-81

-continued

—OCO(CH₂)₄OCH=CH₂    —OCO(CH₂)₄—CH—CH₂
                                    \\O/
  D-82                    D-83

[Structure: 1,3,5-trisubstituted benzene with R groups; R = 5-methyl-3-(2-fluoro-4-X-phenyl)-1,2,4-oxadiazole]

X =  —OCOOC₄H₉    —OCOOC₅H₁₁    —OCOOC₆H₁₃
      D-84          D-85           D-86
—OCOO(CH₂)₂OCOCH=CH₂
  D-87
—OCOO(CH₂)₃OCOCH=CH₂
  D-88
—OCOO(CH₂)₄OCOCH=CH₂
  D-89
—OCOO(CH₂)₅OCOCH=CH₂
  D-90
—OCOO(CH₂)₆OCOCH=CH₂
  D-91
—OCOOCH(CH₃)CH₂CH₂OCOCH=CH₂
  D-92
—OCOOCH(CH₃)CH₂CH₂OCOCH=CH₂
  D-93
—OCOOC(CH₂CH₂O)₂COCH=CH₂
  D-94
—OCOO(CH₂)₂OCOC(CH₃)=CH₂
  D-95
—OCOO(CH₂)₂OCOCH=CHCH₃
  D-96
—OCOO(CH₂)₄OCH=CH₂
  D-97
—OCOO(CH₂)₄—CH—CH₂
              \\O/
  D-98

[Structure: 1,3,5-trisubstituted benzene with R groups; R = 5-methyl-3-(3-fluoro-4-X-phenyl)-1,2,4-oxadiazole]

X =  —OC₄H₉    —OC₅H₁₁    —OC₆H₁₃    —OC₇H₁₅
      D-99       D-100       D-101       D-102
—OC₈H₁₇    —OCH₂CH(CH₃)C₄H₉
  D-103         D-104
—O(CH₂)₂OCOCH=CH₂    —O(CH₂)₃OCOCH=CH₂
  D-105                  D-106
—O(CH₂)₄OCOCH=CH₂    —O(CH₂)₅OCOCH=CH₂
  D-107                  D-108

-continued

—O(CH₂)₆OCOCH=CH₂    —O(CH₂)₇OCOCH=CH₂
D-109                D-110
—O(CH₂)₈OCOCH=CH₂
D-111
—O(CH₂)₂CH(CH₃)OCOCH=CH₂
D-112
—O(CH₂)₃CH(CH₃)OCOCH=CH₂
D-113
—O(CH₂CH₂O)₂COCH=CH₂    —O(CH₂)₄OCOC(CH₃)=CH₂
D-114                   D-115
—O(CH₂)₄OCOCH=CHCH₃    —O(CH₂)₄OCH=CH₂
D-116                  D-117
—O(CH₂)₄—CH—CH₂
              \\O/
D-118

[Structure: 1,3,5-trisubstituted benzene with R groups; R = 5-methyl-3-(3-fluoro-4-X-phenyl)-1,2,4-oxadiazole]

X =  —OCOC₄H₉    —OCOC₅H₁₁    —OCOC₆H₁₃
      D-119       D-120        D-121
—OCO(CH₂)₂OCOCH=CH₂
D-122
—OCO(CH₂)₃OCOCH=CH₂
D-123
—OCO(CH₂)₄OCOCH=CH₂
D-124
—OCO(CH₂)₅OCOCH=CH₂
D-125
—OCO(CH₂)₆OCOCH=CH₂
D-126
—OCO(CH₂)₇OCOCH=CH₂
D-127
—OCO(CH₂)₂CH(CH₃)OCOCH=CH₂
D-128
—OCO(CH₂)₂OCOC(CH₃)=CH₂
D-129
—OCO(CH₂)₂OCOCH=CHCH₃
D-130
—OCO(CH₂)₄OCH=CH₂    —OCO(CH₂)₄—CH—CH₂
D-131                                \\O/
                                   D-132

[Structure: 1,3,5-trisubstituted benzene with R groups; R = 5-methyl-3-(3-fluoro-4-X-phenyl)-1,2,4-oxadiazole]

X =  —OCOOC₄H₉    —OCOOC₅H₁₁    —OCOOC₆H₁₃
      D-133       D-134         D-135
—OCOO(CH₂)₂OCOCH=CH₂
D-136
—OCOO(CH₂)₃OCOCH=CH₂
D-137
—OCOO(CH₂)₄OCOCH=CH₂
D-138
—OCOO(CH₂)₅OCOCH=CH₂
D-139
—OCOO(CH₂)₆OCOCH=CH₂
D-140
—OCOO(CH₂)₇OCOCH=CH₂
D-141
—OCOOCH(CH₃)CH₂CH₂OCOCH=CH₂
D-142
—OCOOC(CH₂CH₂O)₂COCH=CH₂
D-143
—OCOO(CH₂)₂OCOC(CH₃)=CH₂
D-144
—OCOO(CH₂)₂OCOCH=CHCH₃
D-145
—OCOO(CH₂)₄OCH=CH₂
D-146
—OCOO(CH₂)₄—CH—CH₂
              \\O/
D-147

[Structure: 1,3,5-trisubstituted benzene with R groups; R = 5-methyl-3-(3-chloro-4-X-phenyl)-1,2,4-oxadiazole]

X =  —OC₆H₁₃    —OCOC₅H₁₁    —OCOOC₄H₉
      D-148     D-149         D-150
—O(CH₂)₄OCOCH=CH₂    —O(CH₂)₆OCOCH=CH₂
D-151                 D-152
—OCO(CH₂)₃OCOCH=CH₂
D-153
—OCO(CH₂)₄OCOCH=CH₂
D-154
—OCOO(CH₂)₂OCOCH=CH₂
D-155
—OCOO(CH₂)₄OCOCH=CH₂
D-156

[Structure: 1,3,5-trisubstituted benzene with R groups; R = 5-methyl-3-(3-bromo-4-X-phenyl)-1,2,4-oxadiazole]

X =  —OC₆H₁₃    —OCOC₅H₁₁    —OCOOC₄H₉
      D-157     D-158         D-159

-continued

| | |
|---|---|
| —O(CH₂)₄OCOCH=CH₂ | —O(CH₂)₆OCOCH=CH₂ |
| D-160 | D-161 |
| —OCO(CH₂)₃OCOCH=CH₂ | |
| D-162 | |
| —OCO(CH₂)₄OCOCH=CH₂ | |
| D-163 | |
| —OCOO(CH₂)₂OCOCH=CH₂ | |
| D-164 | |
| —OCOO(CH₂)₄OCOCH=CH₂ | |
| D-165 | |

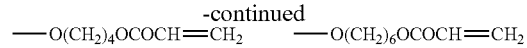

| X = —OC₆H₁₃ | —OCOC₅H₁₁ | —OCOOC₄H₉ |
|---|---|---|
| D-166 | D-167 | D-168 |
| —O(CH₂)₄OCOCH=CH₂ | —O(CH₂)₆OCOCH=CH₂ | |
| D-169 | D-170 | |
| —OCO(CH₂)₃OCOCH=CH₂ | | |
| D-171 | | |
| —OCO(CH₂)₄OCOCH=CH₂ | | |
| D-172 | | |
| —OCOO(CH₂)₂OCOCH=CH₂ | | |
| D-173 | | |
| —OCOO(CH₂)₄OCOCH=CH₂ | | |
| D-174 | | |

| X = —OC₆H₁₃ | —OCOC₅H₁₁ | —OCOOC₄H₉ |
|---|---|---|
| D-175 | D-176 | D-178 |
| —O(CH₂)₄OCOCH=CH₂ | —O(CH₂)₆OCOCH=CH₂ | |
| D-179 | D-180 | |
| —OCO(CH₂)₃OCOCH=CH₂ | | |
| D-181 | | |
| —OCO(CH₂)₄OCOCH=CH₂ | | |
| D-182 | | |
| —OCOO(CH₂)₂OCOCH=CH₂ | | |
| D-183 | | |
| —OCOO(CH₂)₄OCOCH=CH₂ | | |
| D-184 | | |

| X = —OC₆H₁₃ | —OCOC₅H₁₁ | —OCOOC₄H₉ |
|---|---|---|
| D-185 | D-186 | D-187 |

-continued

| | |
|---|---|
| —O(CH₂)₄OCOCH=CH₂ | —O(CH₂)₆OCOCH=CH₂ |
| D-188 | D-189 |
| —OCO(CH₂)₃OCOCH=CH₂ | |
| D-190 | |
| —OCO(CH₂)₄OCOCH=CH₂ | |
| D-191 | |
| —OCOO(CH₂)₂OCOCH=CH₂ | |
| D-192 | |
| —OCOO(CH₂)₄OCOCH=CH₂ | |
| D-193 | |

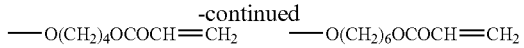

| X = —OC₆H₁₃ | —OCOC₅H₁₁ | —OCOOC₄H₉ |
|---|---|---|
| D-194 | D-195 | D-196 |
| —O(CH₂)₄OCOCH=CH₂ | —O(CH₂)₆OCOCH=CH₂ | |
| D-197 | D-198 | |
| —OCO(CH₂)₃OCOCH=CH₂ | | |
| D-199 | | |
| —OCO(CH₂)₄OCOCH=CH₂ | | |
| D-200 | | |
| —OCOO(CH₂)₂OCOCH=CH₂ | | |
| D-201 | | |
| —OCOO(CH₂)₄OCOCH=CH₂ | | |
| D-202 | | |

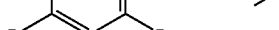

| X = —OC₆H₁₃ | —OCOC₅H₁₁ | —OCOOC₄H₉ |
|---|---|---|
| D-203 | D-204 | D-205 |
| —O(CH₂)₄OCOCH=CH₂ | —O(CH₂)₆OCOCH=CH₂ | |
| D-206 | D-207 | |
| —OCO(CH₂)₃OCOCH=CH₂ | | |
| D-208 | | |
| —OCO(CH₂)₄OCOCH=CH₂ | | |
| D-209 | | |
| —OCOO(CH₂)₂OCOCH=CH₂ | | |
| D-210 | | |
| —OCOO(CH₂)₄OCOCH=CH₂ | | |
| D-211 | | |

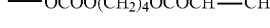

| X = —OC₆H₁₃ | —OCOC₅H₁₁ | —OCOOC₄H₉ |
|---|---|---|
| D-212 | D-213 | D-214 |
| —O(CH₂)₄OCOCH=CH₂ | —O(CH₂)₆OCOCH=CH₂ | |
| D-215 | D-216 | |

-continued

—OCO(CH$_2$)$_3$OCOCH=CH$_2$
D-217
—OCO(CH$_2$)$_4$OCOCH=CH$_2$
D-218
—OCOO(CH$_2$)$_2$OCOCH=CH$_2$
D-219
—OCOO(CH$_2$)$_4$OCOCH=CH$_2$
D-220

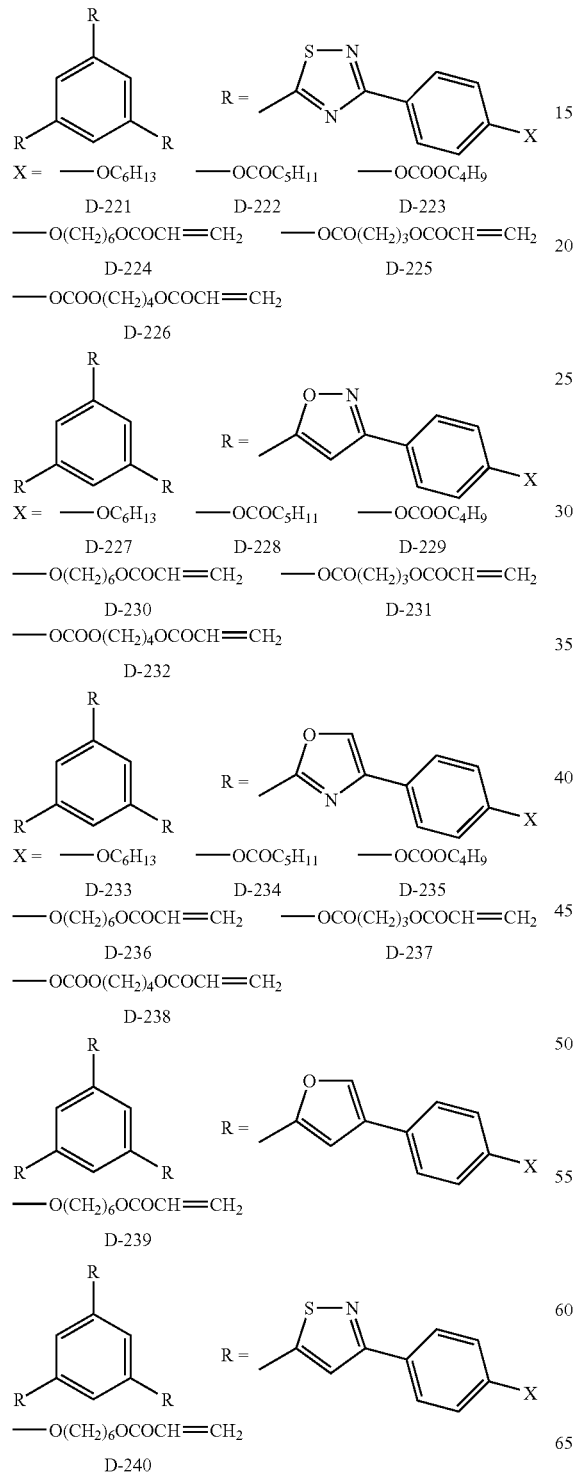

X= —OC$_6$H$_{13}$  —OCOC$_5$H$_{11}$  —OCOOC$_4$H$_9$
   D-221      D-222        D-223
—O(CH$_2$)$_6$OCOCH=CH$_2$  —OCO(CH$_2$)$_3$OCOCH=CH$_2$
   D-224                      D-225
—OCOO(CH$_2$)$_4$OCOCH=CH$_2$
D-226

X= —OC$_6$H$_{13}$  —OCOC$_5$H$_{11}$  —OCOOC$_4$H$_9$
   D-227      D-228        D-229
—O(CH$_2$)$_6$OCOCH=CH$_2$  —OCO(CH$_2$)$_3$OCOCH=CH$_2$
   D-230                      D-231
—OCOO(CH$_2$)$_4$OCOCH=CH$_2$
D-232

X= —OC$_6$H$_{13}$  —OCOC$_5$H$_{11}$  —OCOOC$_4$H$_9$
   D-233      D-234        D-235
—O(CH$_2$)$_6$OCOCH=CH$_2$  —OCO(CH$_2$)$_3$OCOCH=CH$_2$
   D-236                      D-237
—OCOO(CH$_2$)$_4$OCOCH=CH$_2$
D-238

—O(CH$_2$)$_6$OCOCH=CH$_2$
D-239

—O(CH$_2$)$_6$OCOCH=CH$_2$
D-240

-continued

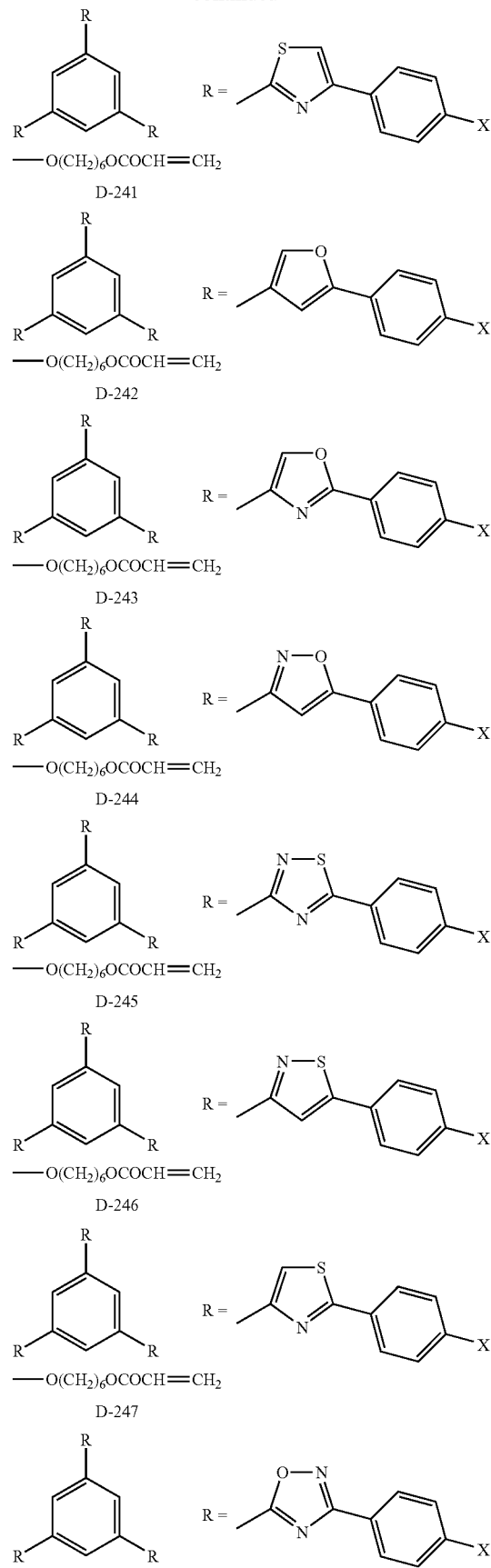

—O(CH$_2$)$_6$OCOCH=CH$_2$
D-241

—O(CH$_2$)$_6$OCOCH=CH$_2$
D-242

—O(CH$_2$)$_6$OCOCH=CH$_2$
D-243

—O(CH$_2$)$_6$OCOCH=CH$_2$
D-244

—O(CH$_2$)$_6$OCOCH=CH$_2$
D-245

—O(CH$_2$)$_6$OCOCH=CH$_2$
D-246

—O(CH$_2$)$_6$OCOCH=CH$_2$
D-247

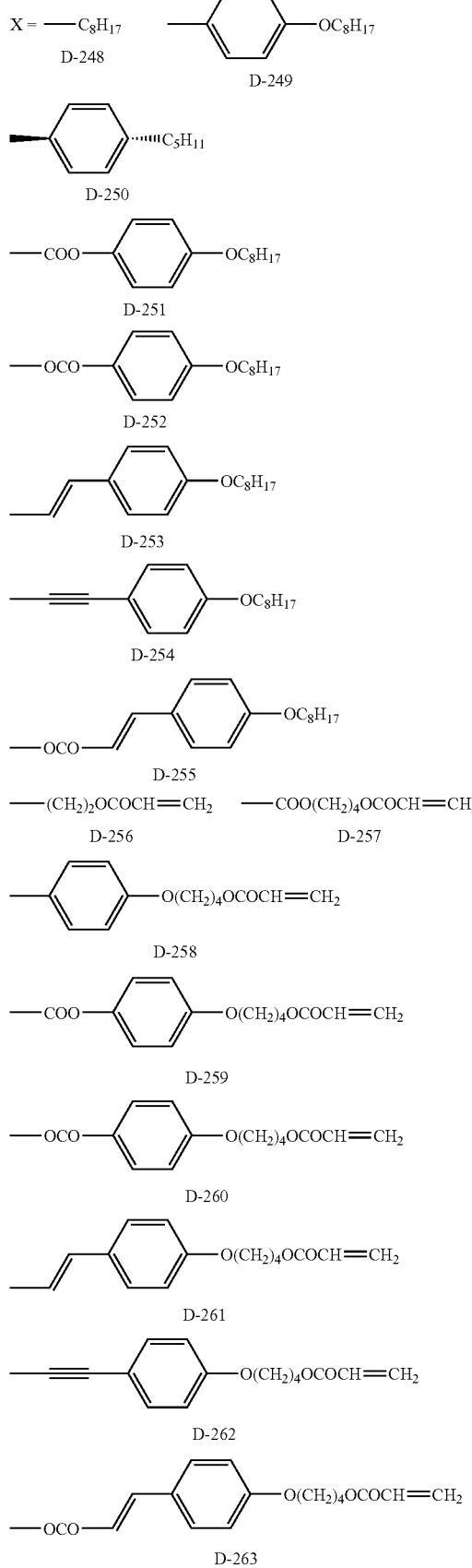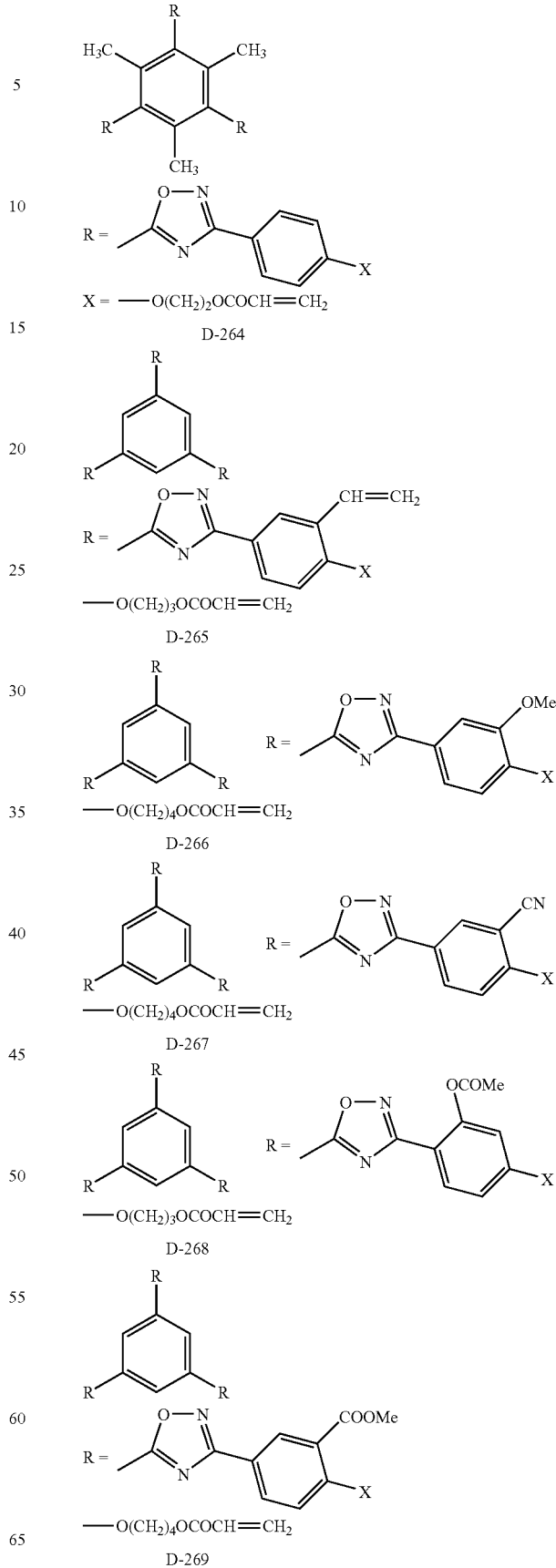

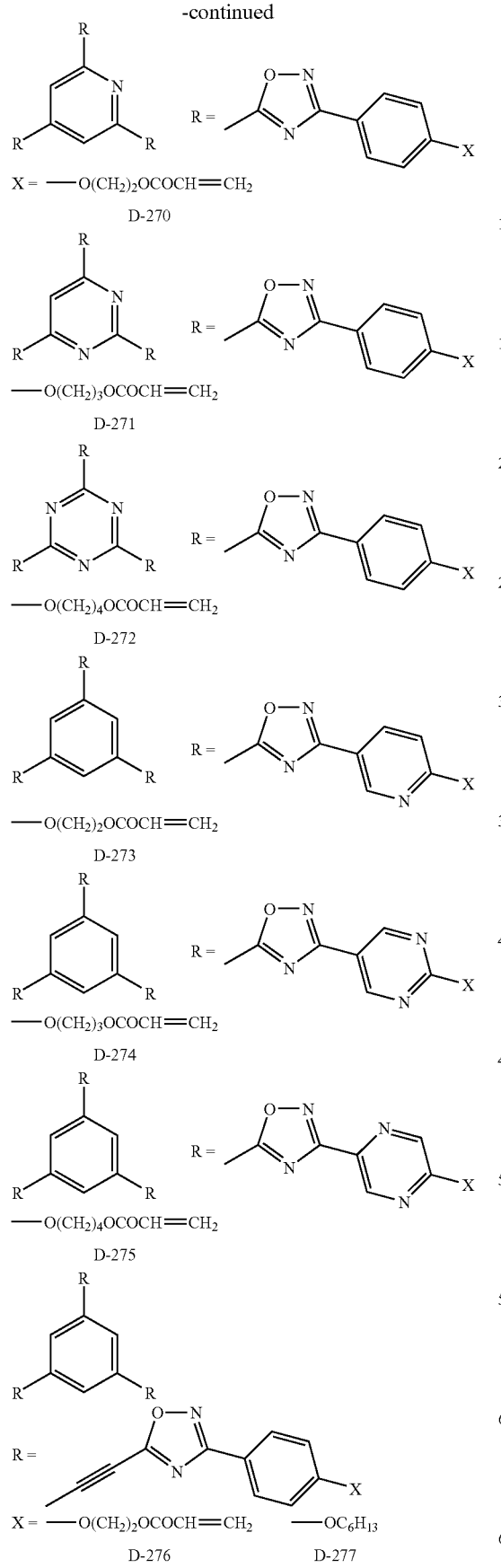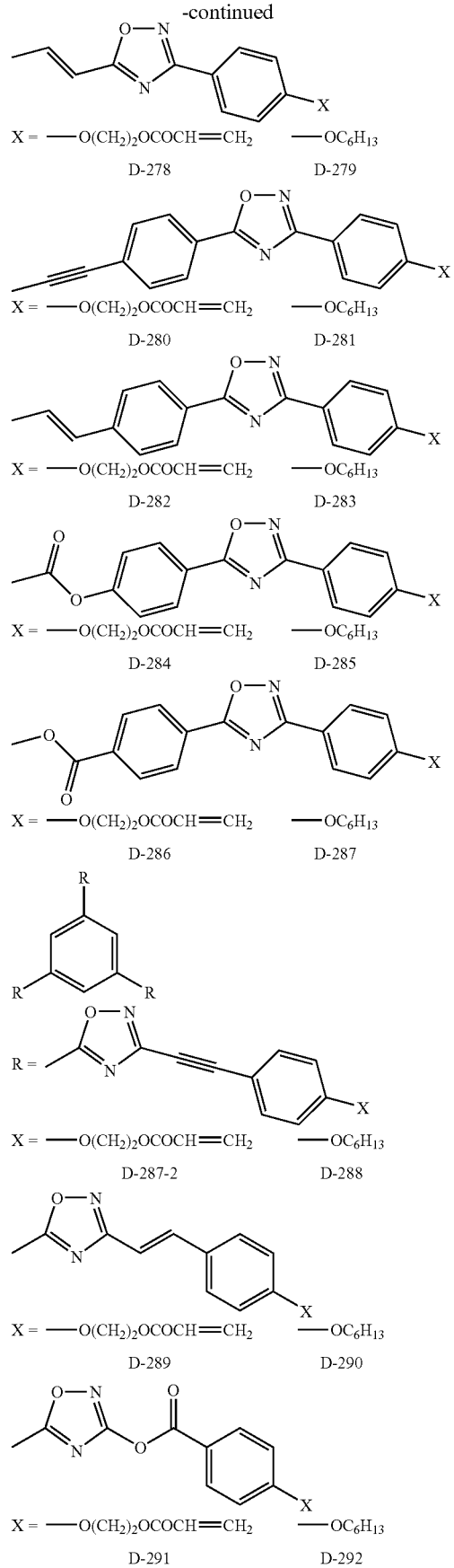

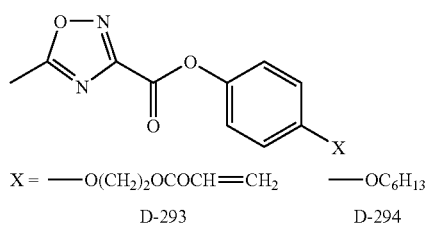

X = —O(CH₂)₂OCOCH=CH₂     —OC₆H₁₃
D-293     D-294

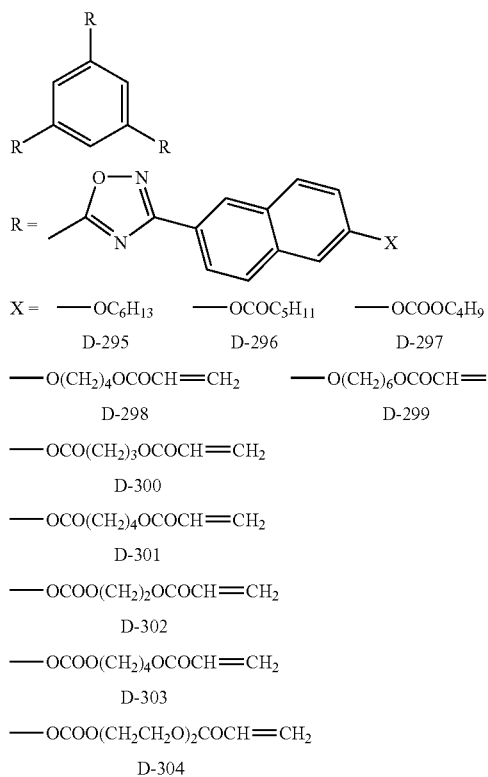

X = —OC₆H₁₃    —OCOC₅H₁₁    —OCOOC₄H₉
D-295    D-296    D-297
—O(CH₂)₄OCOCH=CH₂    —O(CH₂)₆OCOCH=CH₂
D-298    D-299
—OCO(CH₂)₃OCOCH=CH₂
D-300
—OCO(CH₂)₄OCOCH=CH₂
D-301
—OCOO(CH₂)₂OCOCH=CH₂
D-302
—OCOO(CH₂)₄OCOCH=CH₂
D-303
—OCOO(CH₂CH₂O)₂COCH=CH₂
D-304

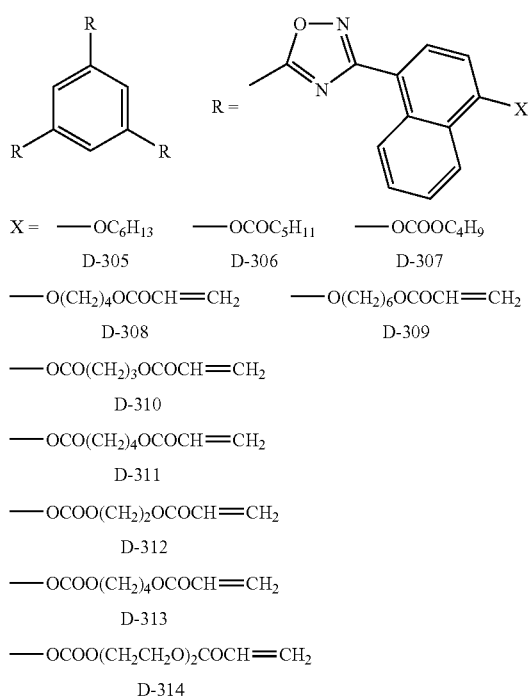

X = —OC₆H₁₃    —OCOC₅H₁₁    —OCOOC₄H₉
D-305    D-306    D-307
—O(CH₂)₄OCOCH=CH₂    —O(CH₂)₆OCOCH=CH₂
D-308    D-309
—OCO(CH₂)₃OCOCH=CH₂
D-310
—OCO(CH₂)₄OCOCH=CH₂
D-311
—OCOO(CH₂)₂OCOCH=CH₂
D-312
—OCOO(CH₂)₄OCOCH=CH₂
D-313
—OCOO(CH₂CH₂O)₂COCH=CH₂
D-314

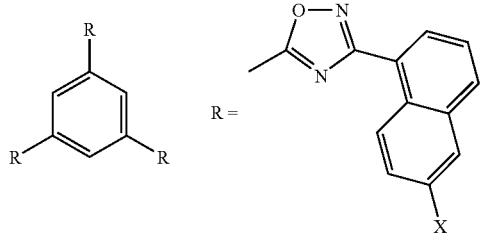

X = —OC₆H₁₃    —OCOC₅H₁₁    —OCOOC₄H₉
D-315    D-316    D-317
—O(CH₂)₄OCOCH=CH₂    —O(CH₂)₆OCOCH=CH₂
D-318    D-319
—OCO(CH₂)₃OCOCH=CH₂
D-320
—OCO(CH₂)₄OCOCH=CH₂
D-321
—OCOO(CH₂)₂OCOCH=CH₂
D-322
—OCOO(CH₂)₄OCOCH=CH₂
D-323
—OCOO(CH₂CH₂O)₂COCH=CH₂
D-324

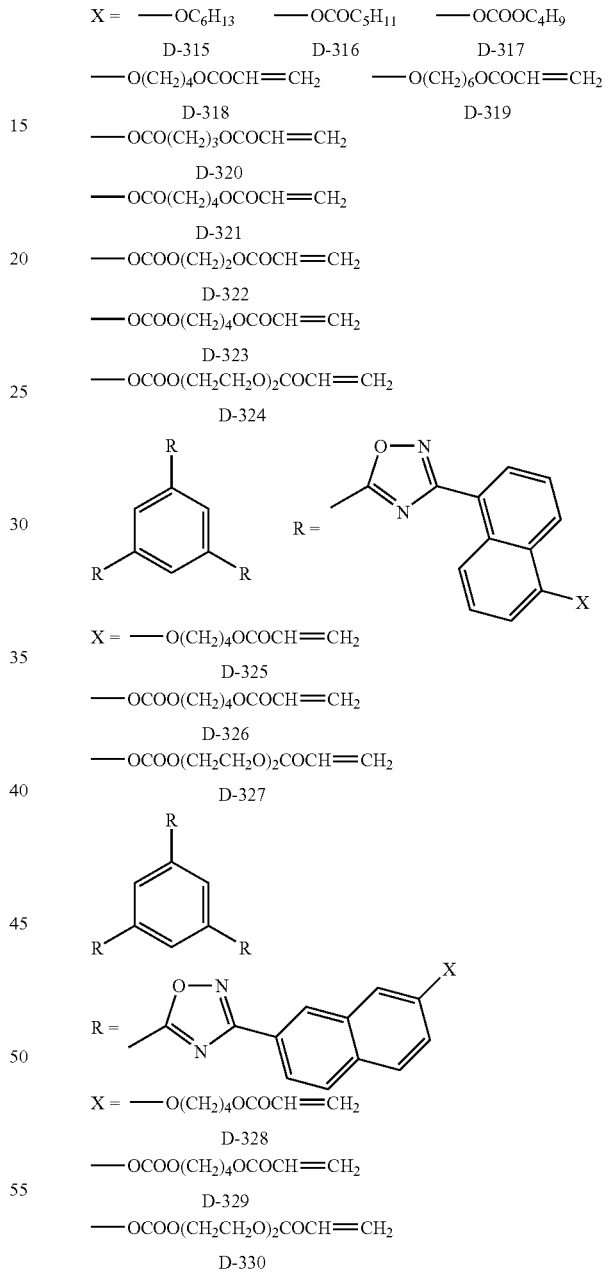

X = —O(CH₂)₄OCOCH=CH₂
D-325
—OCOO(CH₂)₄OCOCH=CH₂
D-326
—OCOO(CH₂CH₂O)₂COCH=CH₂
D-327

X = —O(CH₂)₄OCOCH=CH₂
D-328
—OCOO(CH₂)₄OCOCH=CH₂
D-329
—OCOO(CH₂CH₂O)₂COCH=CH₂
D-330

The uniform alignment as referred to herein is meant to indicate uniform monodomain alignment with no defect. To realize the alignment state, preferred is a liquid phase showing a good monodomain state. A liquid phase having a bad monodomain state may have a polydomain structure, in which the interface between the domains may have an alignment defect and may therefore scatter light. When a liquid phase having a good monodomain state is used, for example in a retarder, then the resulting retarder may readily have a high light transmittance.

The liquid phase which the liquid-crystalline compound of the invention may express includes a columnar phase and a discotic nematic phase ($N_D$ phase). Of those liquid-crystal phases, preferred is a discotic nematic phase ($N_D$ phase) that shows a good monodomain state.

Preferably, the liquid-crystalline compound of the invention expresses a liquid-crystal phase within a range of from 20° C. to 300° C., more preferably from 40° C. to 280° C., most preferably from 60° C. to 250° C. The wording that the compound expresses a liquid phase within a range of from 20° C. to 300° C. is meant to indicate that the liquid-crystal temperature range of the compound broadly covers around 20° C. (concretely, for example, from 10° C. to 22° C.) and around 300° C. (concretely, for example, from 298° C. to 310° C.) and between them. The same shall apply to the range of from 40° C. to 280° C. and to the range of from 60° C. to 250° C.

For obtaining a thin film of uniform alignment of the invention, some additive may be optionally added to the liquid-crystalline compound to prepare a liquid-crystalline composition, and the resulting liquid-crystalline composition may be applied onto a substrate and uniformly aligned thereon to have a liquid-crystal state. Examples of the additive that may be added to the liquid-crystalline compound are air-interface alignment-controlling agent, cissing inhibitor, polymerization initiator and polymerizable monomer.

For realizing the uniform alignment of the thin film, it is desirable that an orientation film is provided on the thin film. However, when the optical axis direction of the discotic liquid-crystalline compound is in parallel to the normal line direction of the thin film surface (homeotropic alignment), the orientation film is not always necessary.

The orientation film may be provided by a method of rubbing treatment of an organic compound (preferably a polymer), a method of oblique vapor deposition of an inorganic compound, a method of formation of a layer having microgrooves, or a method of accumulation of an organic compound (e.g., ω-tricosanoic acid, methyl stearate) according to a Langmuir-Blodgett's technique (LB film). Further, also known is an orientation film that may have an orientation function through electric field application thereto, magnetic field application thereto or light irradiation thereto.

The orientation film may be any and every layer capable of imparting a desired alignment to the liquid-crystalline composition of the invention. In the invention, however, preferred is an orientation film capable of being formed through rubbing treatment or light irradiation. Especially preferred is an orientation film that may be formed through polymer rubbing treatment. In general, the rubbing treatment may be effected by rubbing the surface of a polymer layer a few times with paper or cloth in a predetermined direction. Preferably, in the invention, the rubbing treatment is effected according to the method described in Handbook of Liquid Crystals (by Maruzen). Preferably, the thickness of the orientation film is from 0.01 to 10 μm, more preferably from 0.05 to 3 μm.

One typical and preferred embodiment of the fixed alignment as referred to herein is that the aligned state of liquid-crystalline compounds is kept long as such, but this is not limitatively interpreted. Under ordinary conditions, a temperature range of from 0° C. to 50° C. is preferred; and under severer conditions, a temperature range of from −30° C. to 70° C. is preferred. Within the temperature range, the fixed liquid-crystal composition loses flowability and its alignment state does not change owing to the external field condition or the external force applied to the composition, and therefore, the fixed alignment of the liquid-crystalline compounds can be kept stably as such for long. When an optically-anisotropic layer of which the alignment state has been finally fixed is formed of the liquid-crystalline composition of the invention, then the composition may no more exhibit liquid crystallinity. For example, since a polymerizable group-having compound is used as the liquid-crystalline compound, the compound may be finally polymerized and crosslinked through reaction under heat or light and, as a result, the compound could be a polymer therefore losing its liquid crystallinity.

Examples of the additive that may be added to the liquid-crystalline composition of the invention for forming an optically-anisotropic layer are air-interface alignment-controlling agent, cissing inhibitor, polymerization initiator and polymerizable monomer.

[Air-Interface Alignment-Controlling Agent]

At an air-interface, the liquid-crystalline composition is aligned at the tilt angle of the air-interface. The tilt angle varies, depending on the type of the liquid-crystalline compound and the type of the additives in the liquid-crystalline composition, and therefore, the tilt angle of the air-interface must be controlled suitably in accordance with the object of the composition.

For controlling the tilt angle, for example, an external field such as an electric field or a magnetic field may be applied to the composition, or an additive may be added to the composition. Preferably, an additive is used. The additive is preferably a compound having at least one substituted or unsubstituted aliphatic group having from 6 to 40 carbon atoms, or substituted or unsubstituted aliphatic-substituted oligosiloxanoxy group in the molecule, more preferably having at least two such groups in the molecule. For example, as the air-interface alignment-controlling agent, usable are hydrophobic excluded volume effect compounds such as those described in JP-A-2002-20363.

The amount of the air-interface alignment-controlling agent to be added to the liquid-crystalline composition of the invention is preferably from 0.001% by mass to 20% by mass, more preferably from 0.01% by mass to 10% by mass, most preferably from 0.1% by mass to 5% by mass of the composition.

[Cissing Inhibitor]

As the cissing inhibitor that is added to the liquid-crystalline composition of the invention for the purpose of preventing the composition from being repelled in its application to a substrate, in general, a polymer compound is preferably used.

The polymer is not specifically defined so far as it does not have any significant negative influence on the tilt angle change or the alignment of the liquid-crystal composition of the invention.

Examples of the polymer are described in JP-A-8-95030. Especially preferred examples of the polymer are cellulose esters. Examples of the cellulose esters are cellulose acetate, cellulose acetate propionate, hydroxypropyl cellulose and cellulose acetate butyrate.

The amount of the polymer to be used for the purpose of cissing inhibition not interfering with the alignment of the liquid-crystalline composition of the invention is generally from 0.1 to 10% by mass, but preferably from 0.1 to 8% by mass, more preferably from 0.1 to 5% by mass of the composition.

[Polymerization Initiator]

For alignment fixation in the invention, for example, the liquid-crystalline compound is once heated at a temperature for liquid-crystal phase formation, and then cooled with its alignment state kept as such, whereby the liquid crystal may be aligned and fixed as such not interfering with the original alignment thereof. The liquid-crystalline composition of the invention that contains a polymerization initiator added thereto may be heated up to a temperature for liquid-crystal phase formation, then polymerized and cooled, whereby the liquid crystal alignment may also be fixed as such. For the alignment fixation in the invention, the latter polymerization method is preferred. The polymerization includes thermal polymerization using a thermal polymerization initiator and a photopolymerization using a photopolymerization initiator and an electron beam irradiation polymerization. For the purpose of preventing the support from being deformed and denatured by heat, herein preferred is photopolymerization or electron beam irradiation polymerization.

Examples of the photopolymerization initiator are α-carbonyl compounds (described in U.S. Pat. Nos. 2,367,661, 2,367,670), acyloin ethers (described in U.S. Pat. No. 2,448, 828), α-hydrocarbon-substituted aromatic acyloin compounds (described in U.S. Pat. No. 2,722,512), polynuclear quinone compounds (described in U.S. Pat. Nos. 3,046,127, 2,951,758), combination of triarylimidazole dimer and p-aminophenyl ketone (described in U.S. Pat. No. 3,549, 367), acridine and phenazine compounds (described in JP-A-60-105667, U.S. Pat. No. 4,239,850) and oxadiazole compounds (described in U.S. Pat. No. 4,212,970).

The amount of the photopolymerization initiator for use herein is preferably from 0.01 to 20% by mass, more preferably from 0.5 to 5% by mass of the solid content of the coating solution for the optically-anisotropic layer.

For light irradiation for polymerization, preferably used are UV rays. The irradiation energy is preferably from 10 mJ/cm$^2$ to 50 J/cm$^2$, more preferably from 50 mJ/cm$^2$ to 800 mJ/cm$^2$. For promoting photopolymerization, the light irradiation may be effected under heat. The oxygen concentration in the atmosphere participates in the degree of polymerization. Therefore, when the desired degree of polymerization could not be attained in air, then it is desirable that the oxygen concentration is lowered according to a method of purging with nitrogen. Preferably, the oxygen concentration is at most 10%, more preferably at most 7%, most preferably at most 3%

[Polymerizable Monomer]

A polymerizable monomer may be added to the liquid-crystalline composition of the invention. The polymerizable monomer usable in the invention is not specifically defined, so far as it is miscible with the liquid-crystalline compound of the invention and it does not significantly detract from the alignment of the liquid-crystalline composition. Preferred are compounds having a polymerizable active ethylenic unsaturated group such as a vinyl group, a vinyloxy group, an acryloyl group or a methacryloyl group. The amount of the polymerizable monomer to be added may be generally from 0.5 to 50% by mass, preferably from 1 to 30% by mass of the liquid-crystalline compound. When a monomer having two or more reactive functional groups is used, it is more preferable since it may be effective for enhancing the adhesiveness between the orientation film and the optically-anisotropic layer.

[Coating Solvent]

The solvent for use in preparing the liquid-crystalline composition of the invention is preferably an organic solvent. Examples of the organic solvent are amides (e.g., N,N-dimethylformamide), sulfoxides (e.g., dimethylsulfoxide) heterocyclic compounds (e.g., pyridine), hydrocarbons (e.g., toluene, hexane), alkyl halides (e.g., chloroform, dichloromethane), esters (e.g., methyl acetate, butyl acetate), ketones (e.g., acetone, methyl ethyl ketone, methyl isobutyl ketone, cyclohexanone), ethers (e.g., tetrahydrofuran, 1,2-dimethoxyethane). Preferred are alkyl halides, esters and ketones. Two or more organic solvents may be used as combined.

[Coating Method]

The thin film of the invention may be formed by preparing a coating solution of the liquid-crystalline composition of the invention by the use of the above-mentioned solvent, the applying the solution onto an orientation film and processing it for alignment of the liquid-crystalline composition. The coating solution may be applied to the film in any known method (for example, according to a wire bar coating method, an extrusion coating method, a direct gravure coating method, a reverse gravure coating method, a die coating method).

The invention is described more concretely with reference to the following Examples. The material, the amount used, the ratio, the treatment and the treatment process shown in the following Examples may be suitably changed and modified not overstepping the scope and the sprit of the invention. Accordingly, the scope of the invention should not be limited by the following Examples.

EXAMPLE 1

[Production of D-3]

D-3 was produced according to the following scheme:

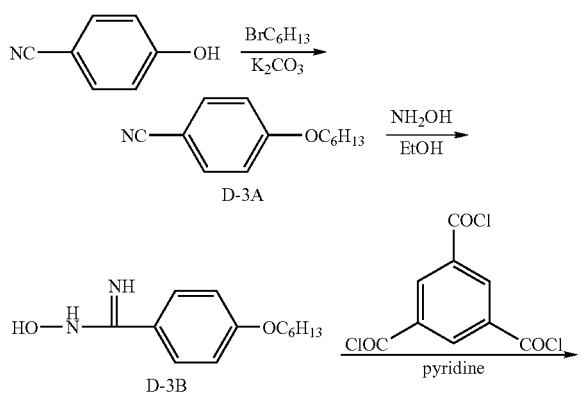

-continued

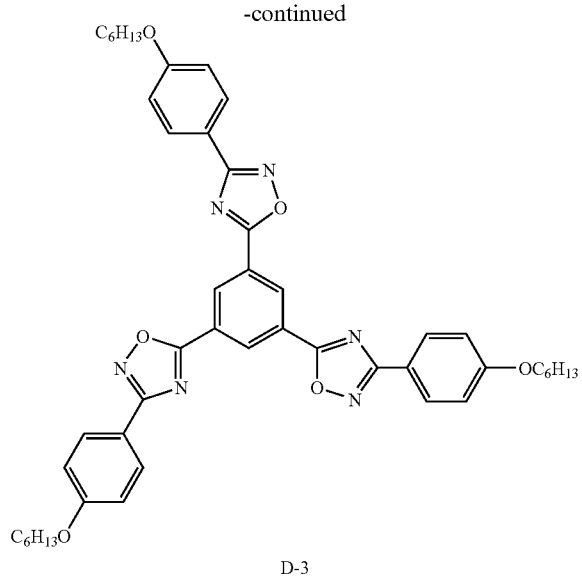

D-3

(Production of D-3A)

15.0 g of 4-cyanophenol was dissolved in 300 ml of dimethylformamide, to which were added 20.9 g of potassium carbonate and 18.5 ml of 1-bromohexane, and then this was stirred under nitrogen atmosphere at 110° C. for 5 hours. Water was added to the reaction solution, and this was then extracted with ethyl acetate and washed with saturated saline. The organic layer was concentrated under reduced pressure, and then purified through column chromatography to obtain 25.0 g of D-3A.

(Production of D-3B)

25.0 g of D-3A was dissolved in 200 ml of ethanol, to which was added 26.0 ml of 50% hydroxylamine solution, and this was then stirred at 90° C. for 3 hours. After cooled, methanol was added to the reaction solution, and the precipitated crystal was taken out through filtration and dried whereby 29.0 g of a crystal, D-3B was obtained.

(Production of D-3)

29.0 g of D-38 was dissolved in 300 ml of 1,4-dioxane, to which were added 10.2 g of trimesic acid chloride and 10.9 ml of pyridine, and this was stirred at 90° C. for 7 hours. After cooled, methanol was added to it, and the precipitated crystal was taken out through filtration. This was purified through column chromatography and 25 g of D-3 was thus obtained. The NMR spectrum of the thus-obtained D-3 was as follows:

$^1$H-NMR (solvent: CDCl$_3$, standard: tetramethylsilane) δ (ppm)

0.85 (9H, t)
1.25-1.35 (12H, m)
1.35-1.45 (6H, m)
1.70-1.80 (6H, m)
3.95 (6H, t)
6.95 (6H, d)
8.05 (6H, d)
9.10 (3H, s)

The phase transition temperature of the thus-obtained D-3 was determined through texture observation with a polarization microscope. First, the temperature was elevated, and the crystal phase of the compound changed to an isotropic liquid phase at around 139° C. Next, the temperature was gradually lowered from 139° C., and at around 123° C., the phase of the compound changed to a discotic nematic phase; and when the temperature was further lowered to 98° C., the phase of the compound again changed to a crystal phase. Specifically, it was found that, while cooled, the compound D-3 exhibits a discotic nematic phase within a temperature range of from 123° C. to 98° C.

EXAMPLE 2

[Production of D-7]

D-7 was produced according to the following scheme:

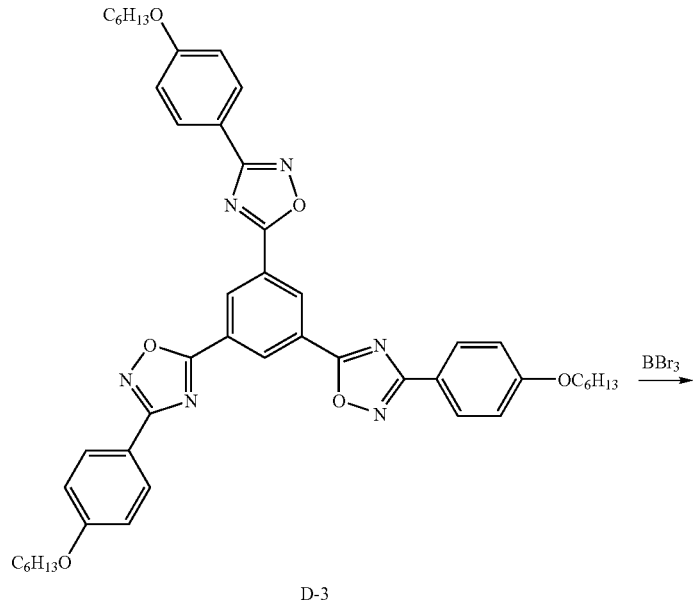

D-3

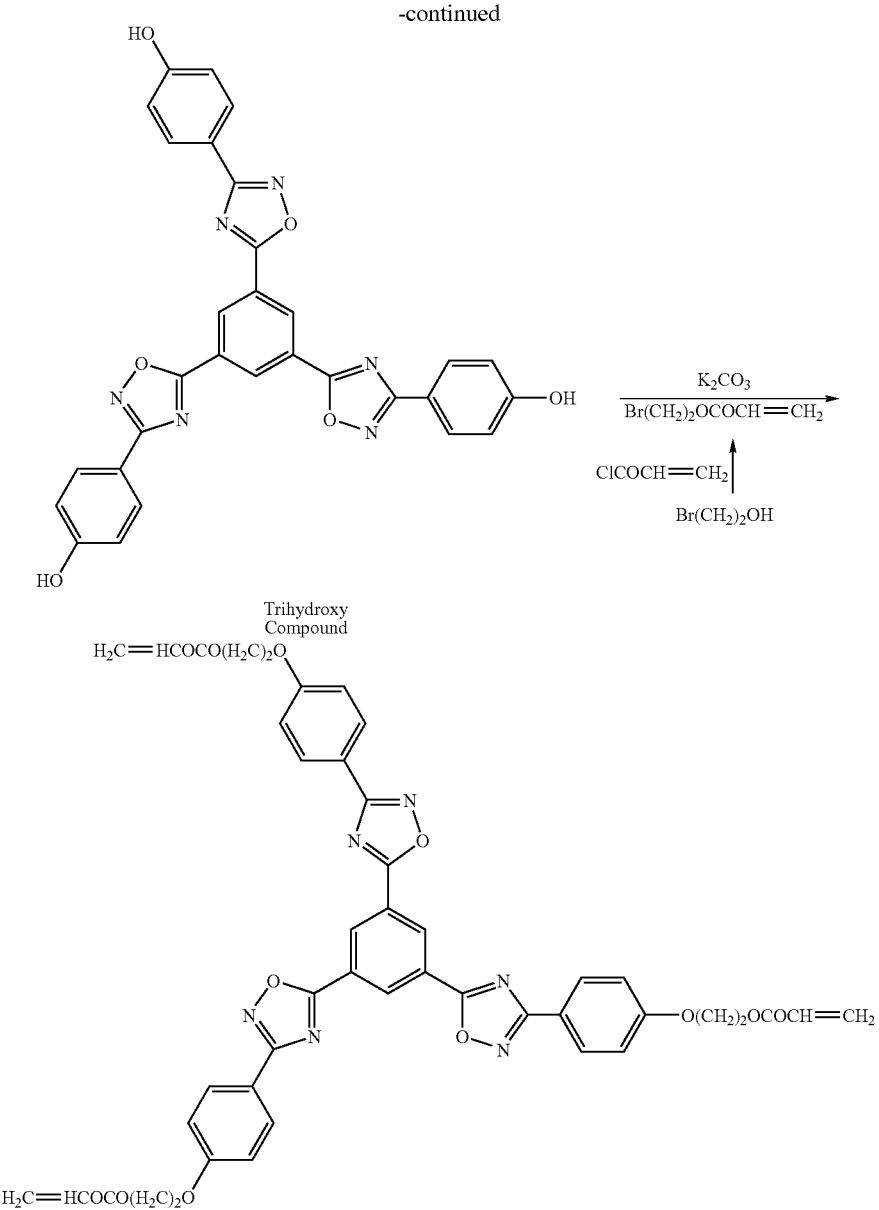

D-7

11.0 g of D-3 was dissolved in 100 ml of CH$_2$Cl$_2$, to which was added 135 ml of boron tribromide (1.0 M CH$_2$Cl$_2$ solution). This was stirred at 40° C. for 8 hours, then water was added to the reaction solution, and the precipitated crystal was taken out through filtration. The crystal was dried to obtain 7.5 g of a trihydroxy compound as above.

0.34 g of 2-bromobutanol was dissolved in 5 ml of dimethylacetamide, to which was dropwise added 0.26 ml of acrylic acid chloride, and this was stirred at room temperature for 1 hour. Then, 20 ml of water and 20 ml of hexane were added to it to wash the organic layer. After liquid-liquid separation, the hexane layer was removed, and 0.3 g of the above trihydroxy compound, 0.44 g of potassium carbonate and 30 ml of dimethylformamide were added to it, and this was stirred at 90° C. for 5 hours. Water was added to the reaction solution and this was extracted with CH$_2$Cl$_2$. The organic layer was concentrated and purified through column chromatography to obtain 0.36 g of a crystal of D-7. The NMR spectrum of the thus-obtained D-7 was as follows:

$^1$H-NMR (solvent: CDCl$_3$, standard: tetramethylsilane) δ (ppm)
4.33 (6H, t)
4.60 (6H, t)
5.89 (3H, dd)
6.20 (3H, dd)
6.50 (3H, dd)
7.05 (6H, d)
8.15 (6H, d)
9.20 (3H, s)

The phase transition temperature of the thus-obtained D-7 was determined through texture observation with a polarization microscope. First, the temperature was elevated, and the crystal phase of the compound changed to an isotropic liquid phase at around 173° C. Next, the temperature was gradually lowered from 173° C., and at around 89° C., the phase of the compound changed to a discotic nematic phase; and when the temperature was further lowered to room temperature, the phase of the compound again changed to a crystal phase. Specifically, it was found that, while cooled, the compound D-7 exhibits a discotic nematic phase within a temperature range of from 89° C. to room temperature.

EXAMPLE 3

[Production of D-8]

D-8 was produced according to the following scheme:

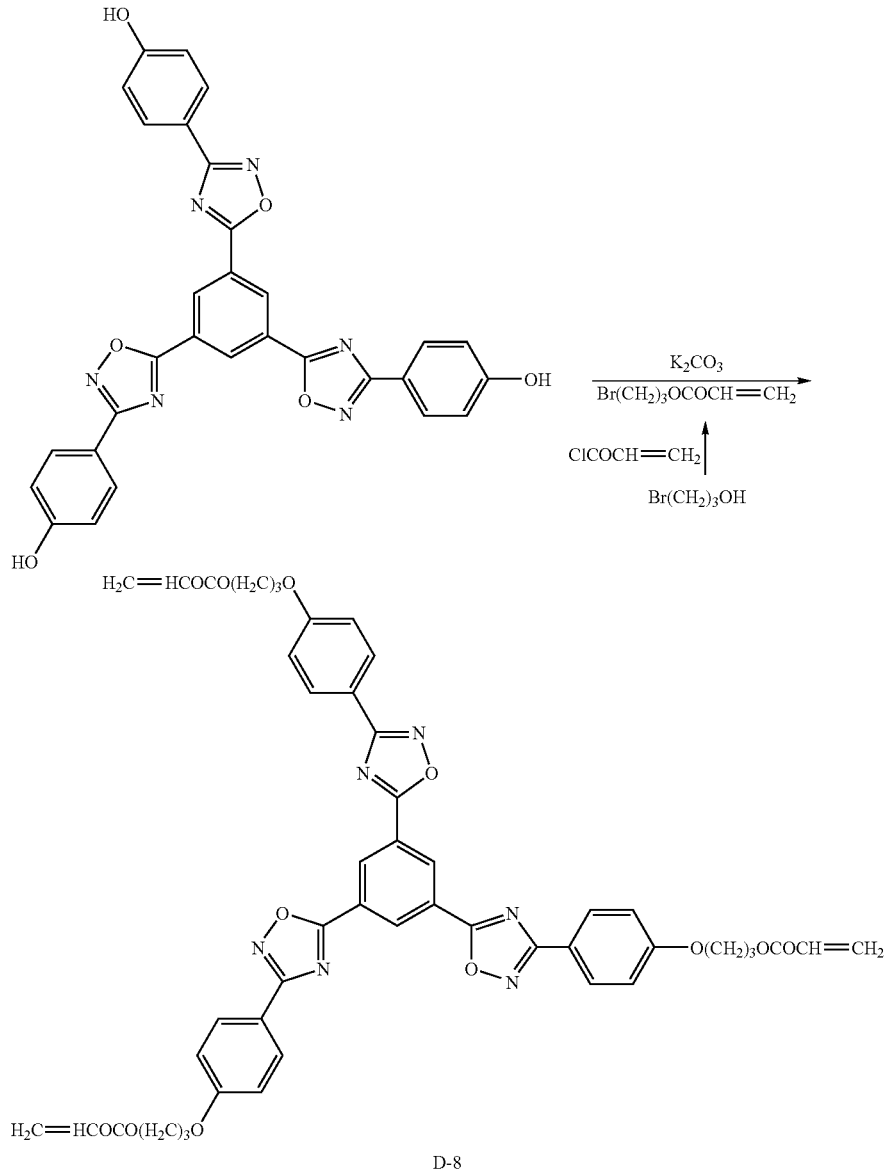

0.3 g of D-8 was obtained according to the same process as in Example 2, for which, however, the starting compound was changed as in the above. The NMR spectrum of the thus-obtained D-8 was as follows:

$^1$H-NMR (solvent: CDCl$_3$, standard: tetramethylsilane) δ (ppm)
2.15-2.25 (6H, m)
4.15 (6H, t)
4.40 (6H, t)
5.85 (3H, dd)
6.25 (3H, dd)
6.45 (3H, dd)
7.05 (6H, d)
8.20 (6H, d)
9.25 (3H, s)

The phase transition temperature of the thus-obtained D-8 was determined through texture observation with a polarization microscope. First, the temperature was elevated, and the crystal phase of the compound changed to an isotropic liquid phase at around 141° C. Next, the temperature was gradually lowered from 141° C., and at around 104° C., the phase of the compound changed to a discotic nematic phase; and when the temperature was further lowered to room temperature, the phase of the compound again changed to a crystal phase. Specifically, it was found that, while cooled, the compound D-8 exhibits a discotic nematic phase within a temperature range of from 104° C. to room temperature.

EXAMPLE 4

[Production of D-9]

D-9 was produced according to the following scheme:

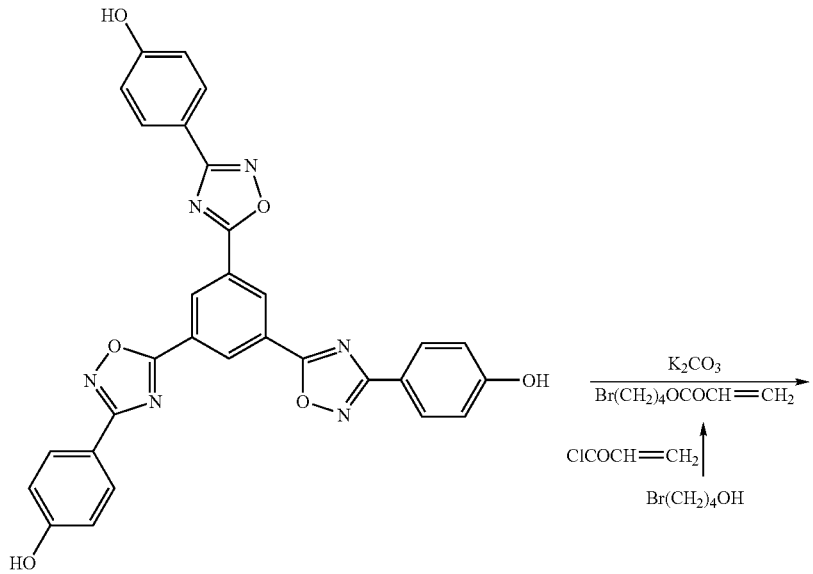

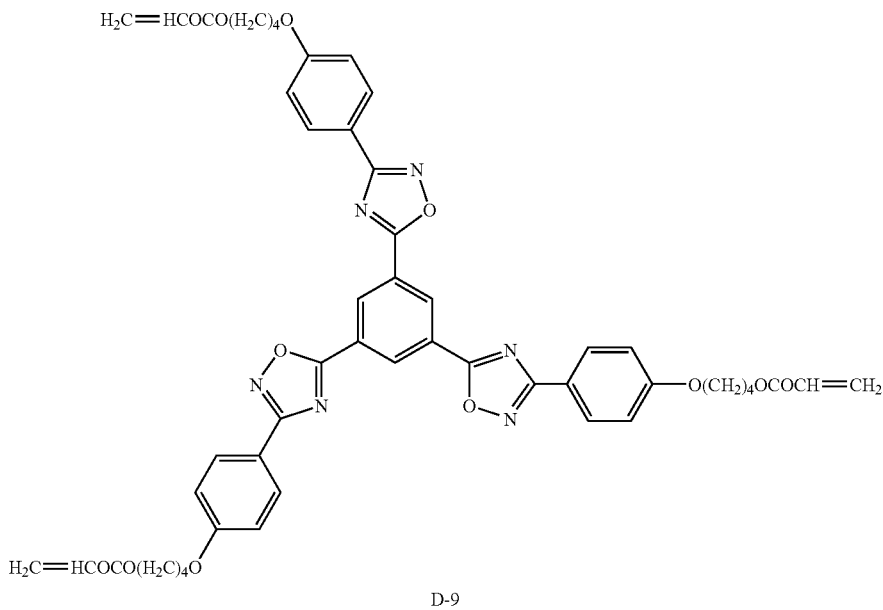

D-9

0.3 g of D-9 was obtained according to the same process as in Example 2, for which, however, the starting compound was changed as in the above. The NMR spectrum of the thus-obtained D-9 was as follows:

$^1$H-NMR (solvent: CDCl$_3$, standard: tetramethylsilane) δ (ppm)

1.90-2.00 (12H, m)
4.10 (6H, t)
4.30 (6H, t)
5.85 (3H, dd)
6.15 (3H, dd)
6.45 (3H, dd)
7.05 (6H, d)
8.15 (6H, d)
9.25 (3H, s)

The phase transition temperature of the thus-obtained D-9 was determined through texture observation with a polarization microscope. First, the temperature was elevated, and the crystal phase of the compound changed to an isotropic liquid phase at around 119° C. Next, the temperature was gradually lowered from 119° C., and at around 106° C., the phase of the compound changed to a discotic nematic phase; and when the temperature was further lowered to 72° C., the phase of the compound again changed to a crystal phase. Specifically, it was found that, while cooled, the compound D-9 exhibits a discotic nematic phase within a temperature range of from 106° C. to 72° C.

EXAMPLE 5

[Production of D-10]

D-10 was produced according to the following scheme:

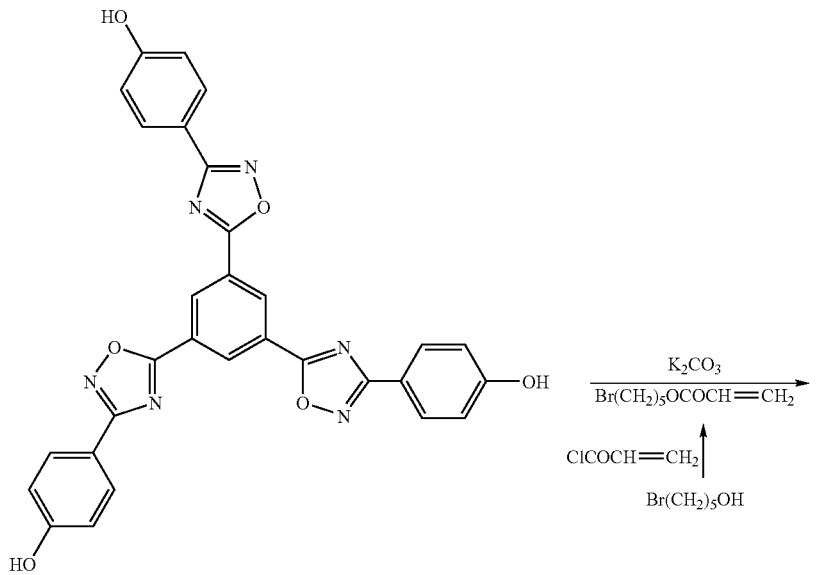

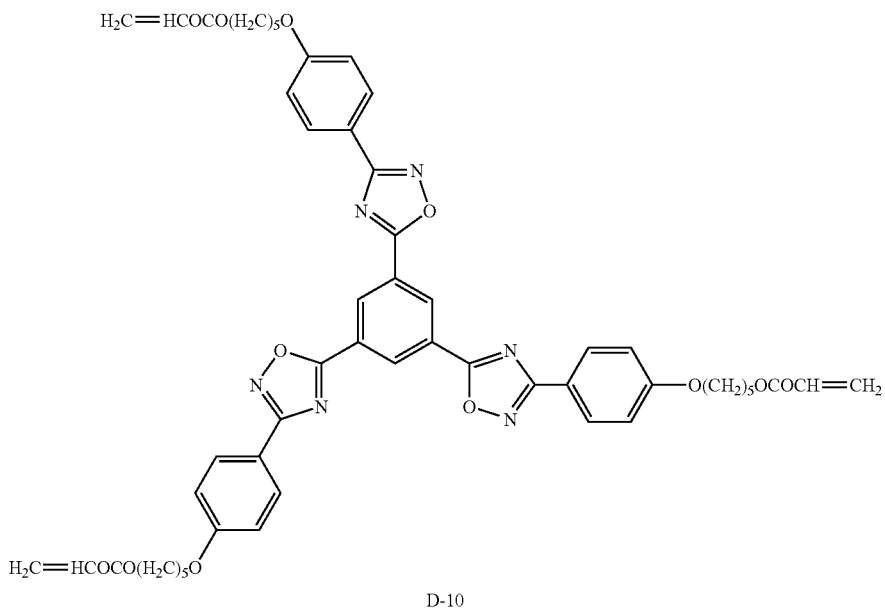

D-10

0.35 g of D-10 was obtained according to the same process as in Example 2, for which, however, the starting compound was changed as in the above. The NMR spectrum of the thus-obtained D-10 was as follows:

$^1$H-NMR (solvent: CDCl$_3$, standard: tetramethylsilane) δ (ppm)
1.55-1.65 (6H, m)
1.75-1.85 (6H, m)
1.85-1.95 (6H, m)
4.05 (6H, t)
4.20 (6H, t)
5.80 (3H, dd)
6.13 (3H, dd)
6.40 (3H, dd)
7.03 (6H, d)
8.15 (6H, d)
9.25 (3H, s)

The phase transition temperature of the thus-obtained D-10 was determined through texture observation with a polarization microscope. First, the temperature was elevated, and the crystal phase of the compound changed to an isotropic liquid phase at around 144° C. Next, the temperature was gradually lowered from 144° C., and at around 106° C., the phase of the compound changed to a discotic nematic phase; and when the temperature was further lowered to 72° C., the phase of the compound again changed to a crystal phase. Specifically, it was found that, while cooled, the compound D-10 exhibits a discotic nematic phase within a temperature range of from 106° C. to 72° C.

EXAMPLE 6

[Production of D-11]

D-11 was produced according to the following scheme:

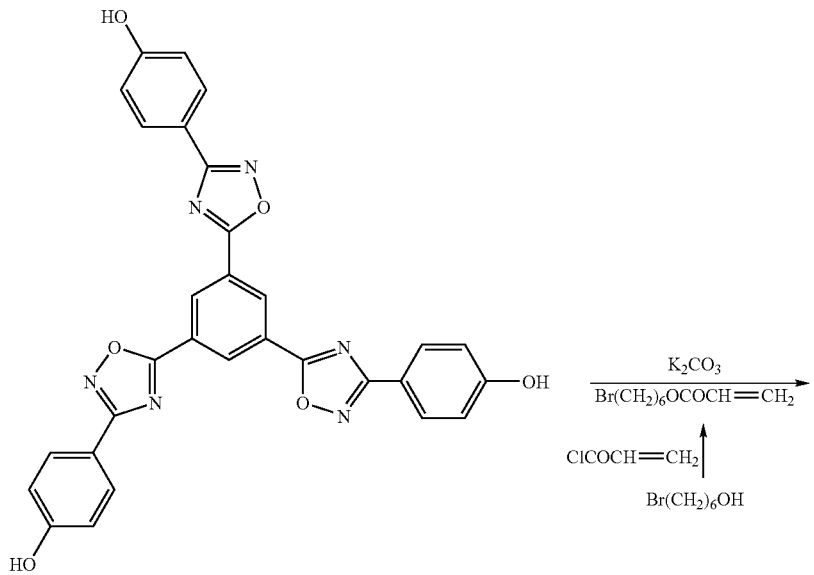

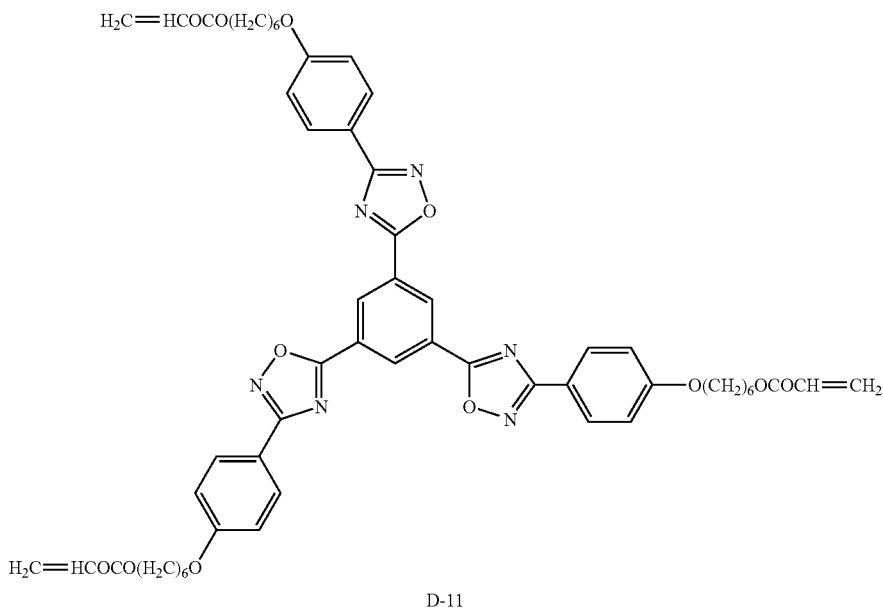

D-11

0.35 g of D-11 was obtained according to the same process as in Example 2, for which, however, the starting compound was changed as in the above. The NMR spectrum of the thus-obtained D-11 was as follows:

$^1$H-NMR (solvent: CDCl$_3$, standard: tetramethylsilane) δ (ppm)
1.40-1.60 (12H, m)
1.70-1.80 (6H, m)
1.80-1.90 (6H, m)
4.05 (6H, t)
4.20 (6H, t)
5.80 (3H, dd)
6.13 (3H, dd)
6.40 (3H, dd)
7.05 (6H, d)
8.15 (6H, d)
9.20 (3H, s)

The phase transition temperature of the thus-obtained D-11 was determined through texture observation with a polarization microscope. First, the temperature was elevated, and the crystal phase of the compound changed to an isotropic liquid phase at around 90° C. Next, the temperature was gradually lowered from 90° C., and at around 87° C., the phase of the compound changed to a discotic nematic phase; and when the temperature was further lowered to room temperature, the phase of the compound again changed to a crystal phase. Specifically, it was found that, while cooled, the compound D-11 exhibits a discotic nematic phase within a temperature range of from 87° C. to room temperature.

EXAMPLE 7

[Production of D-38]

D-38 was produced according to the following scheme:

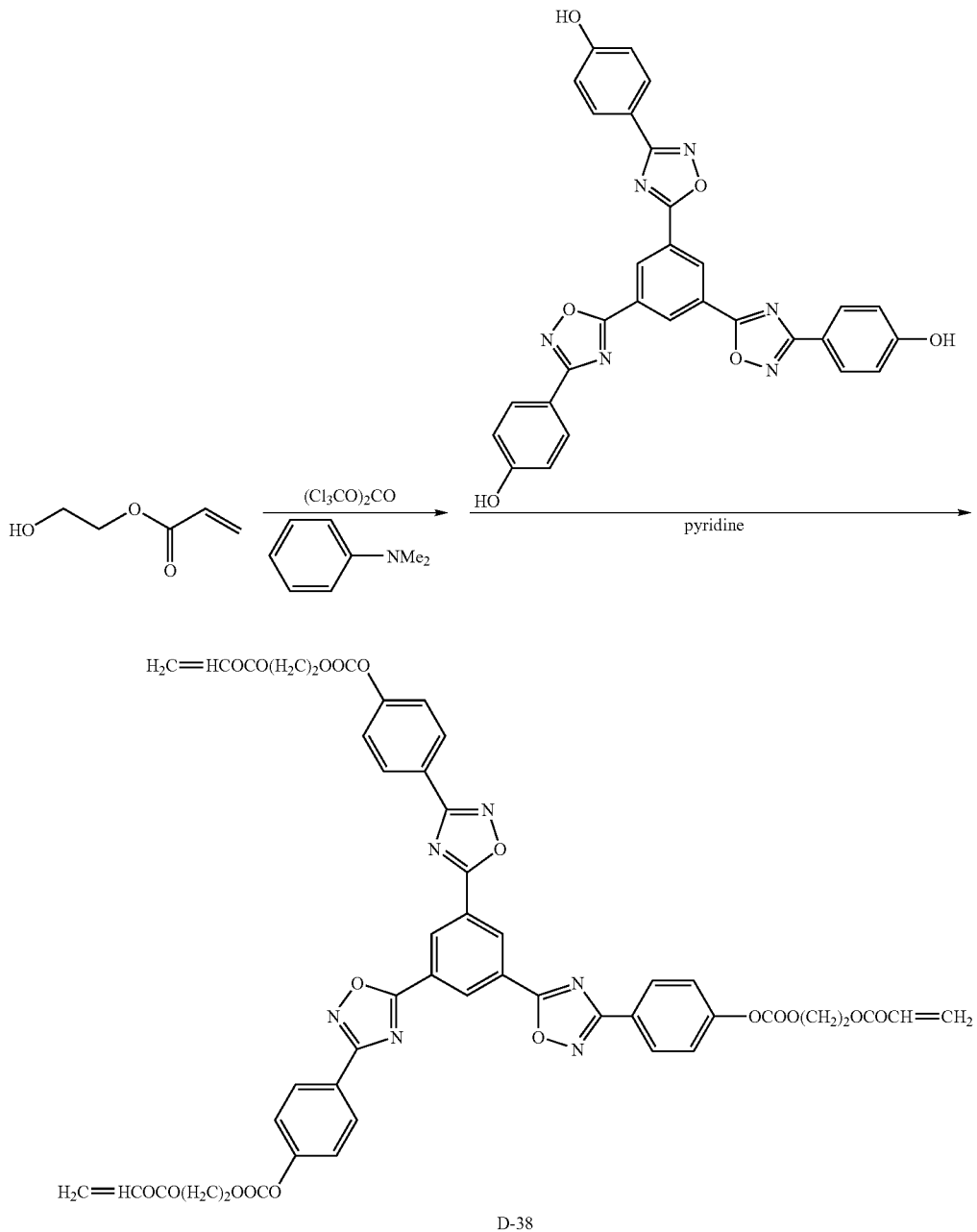

D-38

0.73 g of 2-hydroxyethyl acrylate was dissolved in 10 ml of tetrahydrofuran, and with cooling with ice, 0.84 ml of dimethylaniline was dropwise added thereto, and 0.62 g of triphosgene was added thereto. This was restored to room temperature and stirred for 2 hours, and then with cooling with ice, 0.35 g of a trihydroxy compound as above was added to it. Then, 0.31 ml of pyridine was dropwise added to it, and this was stirred at room temperature for 2 hours. After the reaction, methanol was added to it, and the precipitated crystal was taken out through filtration. This was purified through column chromatography, and 0.38 g of D-38 was thus obtained. The NMR spectrum of the thus-obtained D-38 was as follows:

$^1$H-NMR (solvent: $CDCl_3$, standard: tetramethylsilane) δ (ppm)

4.40-4.60 (12H, m)
5.90 (3H, dd)
6.20 (3H, dd)
6.50 (3H, dd)
7.45 (6H, d)
8.30 (6H, d)
9.30 (3H, s)

The phase transition temperature of the thus-obtained D-38 was determined through texture observation with a polarization microscope. First, the temperature was elevated, and the crystal phase of the compound changed to an isotropic liquid phase at around 114° C. Next, the temperature was gradually lowered from 114° C., and at around 94° C., the phase of the compound changed to a discotic nematic phase; and when the temperature was further lowered to room temperature, the phase of the compound again changed to a crystal phase. Specifically, it was found that, while cooled, the compound D-38 exhibits a discotic nematic phase within a temperature range of from 94° C. to room temperature.

EXAMPLE 8

[Production of D-25]

D-25 was produced according to the following scheme:

13 g of 4-hydroxybutyl acrylate was dissolved in 450 ml of acetone, and with cooling with ice, a solution prepared by adding 180 ml of water and 60 ml of sulfuric acid to chromium trioxide was dropwise added to the resulting solution. This was stirred at room temperature for 5 hours, and then acetone was evaporated away under reduced pressure. Water was added to the reaction solution, and this was extracted with ethyl acetate. The organic layer was concentrated under reduced pressure, and purified through column chromatography to obtain 10.9 g of D-25A. 3.2 g of D-25A was dissolved in 10 ml of toluene, to which were added 4.5 ml of thionyl chloride and a catalytic amount of dimethylformamide, and this was stirred at 40° C. for 20 minutes. Toluene was evaporated away under reduced pressure to obtain D-25B. 0.35 g of a trihydroxy compound as above was dissolved in 10 ml of tetrahydrofuran, to which were added 0.43 ml of diisopropy-

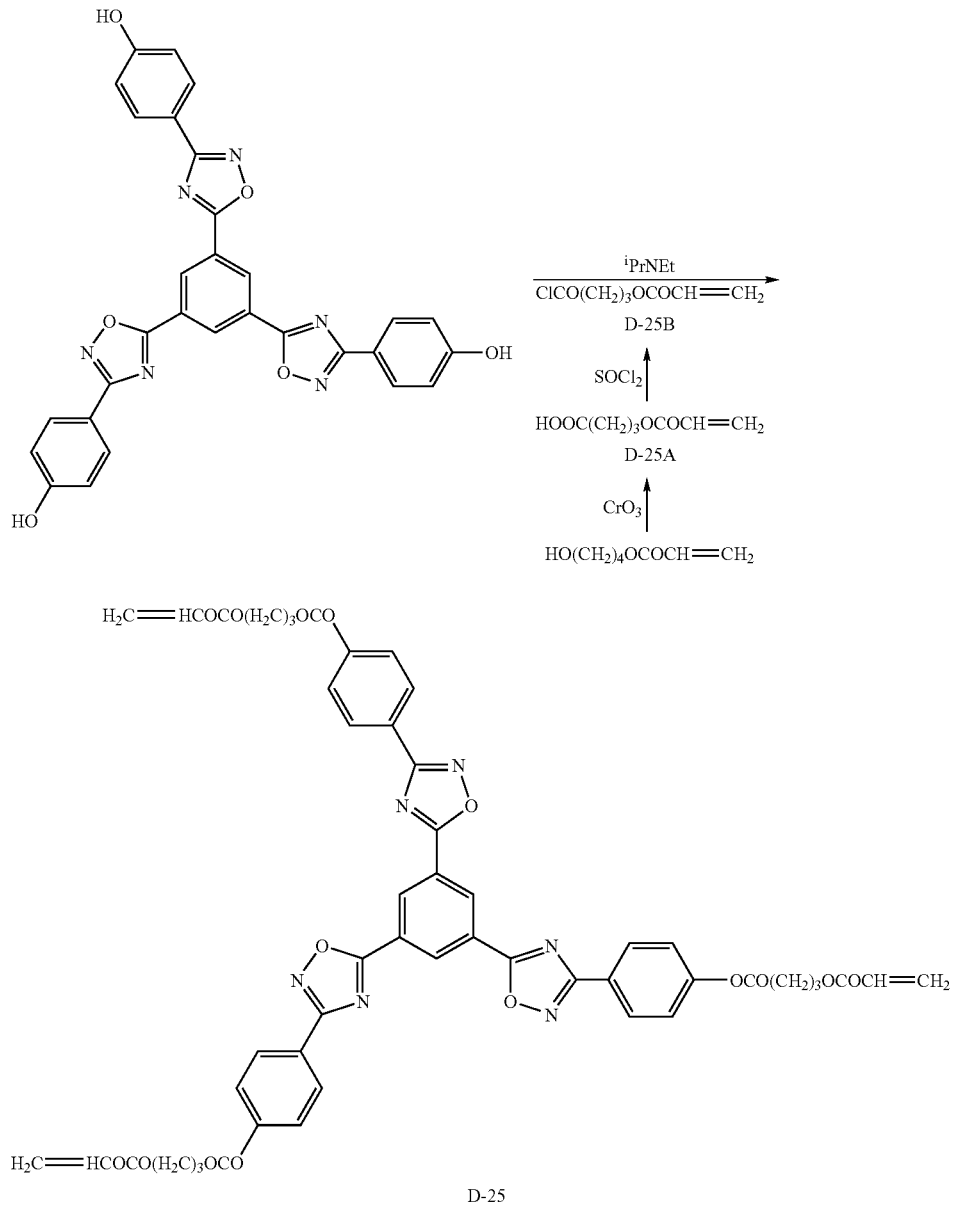

D-25 lethylamine, a catalytic amount of dimethylaminopyridine and 0.88 g of D-25B, and this was stirred at room temperature for 1 hour. After the reaction, methanol was added to it, and the precipitated crystal was taken out through filtration. This was purified through column chromatography to obtain 0.40 g of D-25. The NMR spectrum of the thus-obtained D-25 was as follows:

$^1$H-NMR (solvent: CDCl$_3$, standard: tetramethylsilane) δ (ppm)

2.15-2.25 (6H, m)

2.75 (6H, t)

4.30 (6H, t)

5.85 (3H, dd)

6.25 (3H, dd)

6.45 (3H, dd)

7.30 (6H, d)

8.28 (6H, d)

9.23 (3H, s)

The phase transition temperature of the thus-obtained D-25 was determined through texture observation with a polarization microscope. First, the temperature was elevated, and the crystal phase of the compound changed to an isotropic liquid phase at around 140° C. Next, the temperature was gradually lowered from 140° C., and at around 78° C., the phase of the compound changed to a discotic nematic phase; and when the temperature was further lowered to 69° C., the phase of the compound again changed to a crystal phase. Specifically, it was found that, while cooled, the compound D-25 exhibits a discotic nematic phase within a temperature range of from 78° C. to 69° C.

EXAMPLE 9

[Production of D-52]

D-52 was produced according to the following scheme:

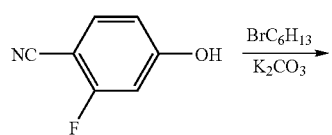

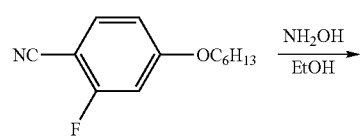

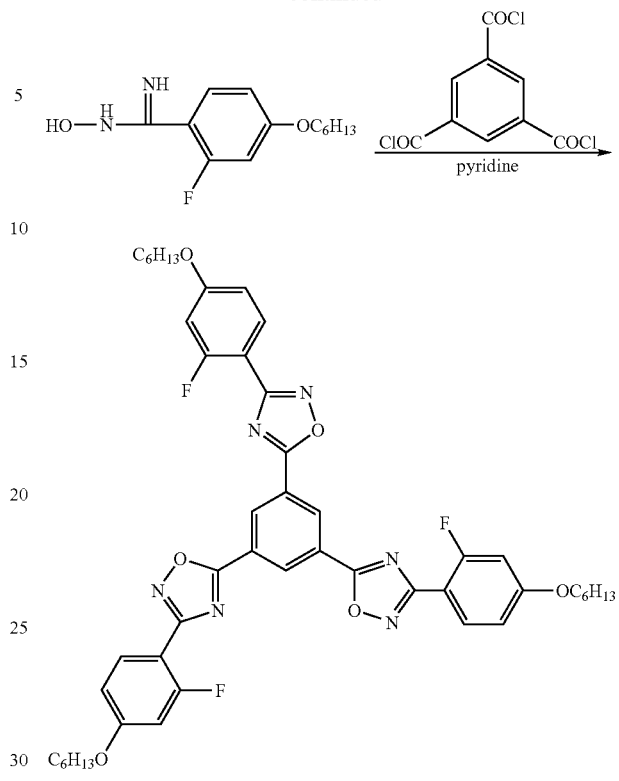

D-52

35 g of D-52 was obtained according to the same process as in Example 1, for which, however, the starting compound was changed as in the above. The NMR spectrum of the thus-obtained D-52 was as follows:

$^1$H-NMR (solvent: CDCl$_3$, standard: tetramethylsilane) δ (ppm)

0.85 (9H, t)

1.25-1.35 (12H, m)

1.35-1.45 (6H, m)

1.70-1.80 (6H, m)

4.10 (6H, t)

6.80 (3H, dd)

6.90 (3H, dd)

8.15 (3H, t)

9.20 (3H, s)

The phase transition temperature of the thus-obtained D-52 was determined through texture observation with a polarization microscope. The temperature was elevated, and the crystal phase of the compound changed to a discotic nematic liquid-crystal phase at around 141° C. At over 142° C., the phase changed to an isotropic liquid phase. Specifically, it was found that D-52 exhibits a discotic nematic liquid-crystal phase within a temperature range of from 141° C. to 142° C.

EXAMPLE 10
[Production of D-58]
D-58 was produced according to the following scheme:
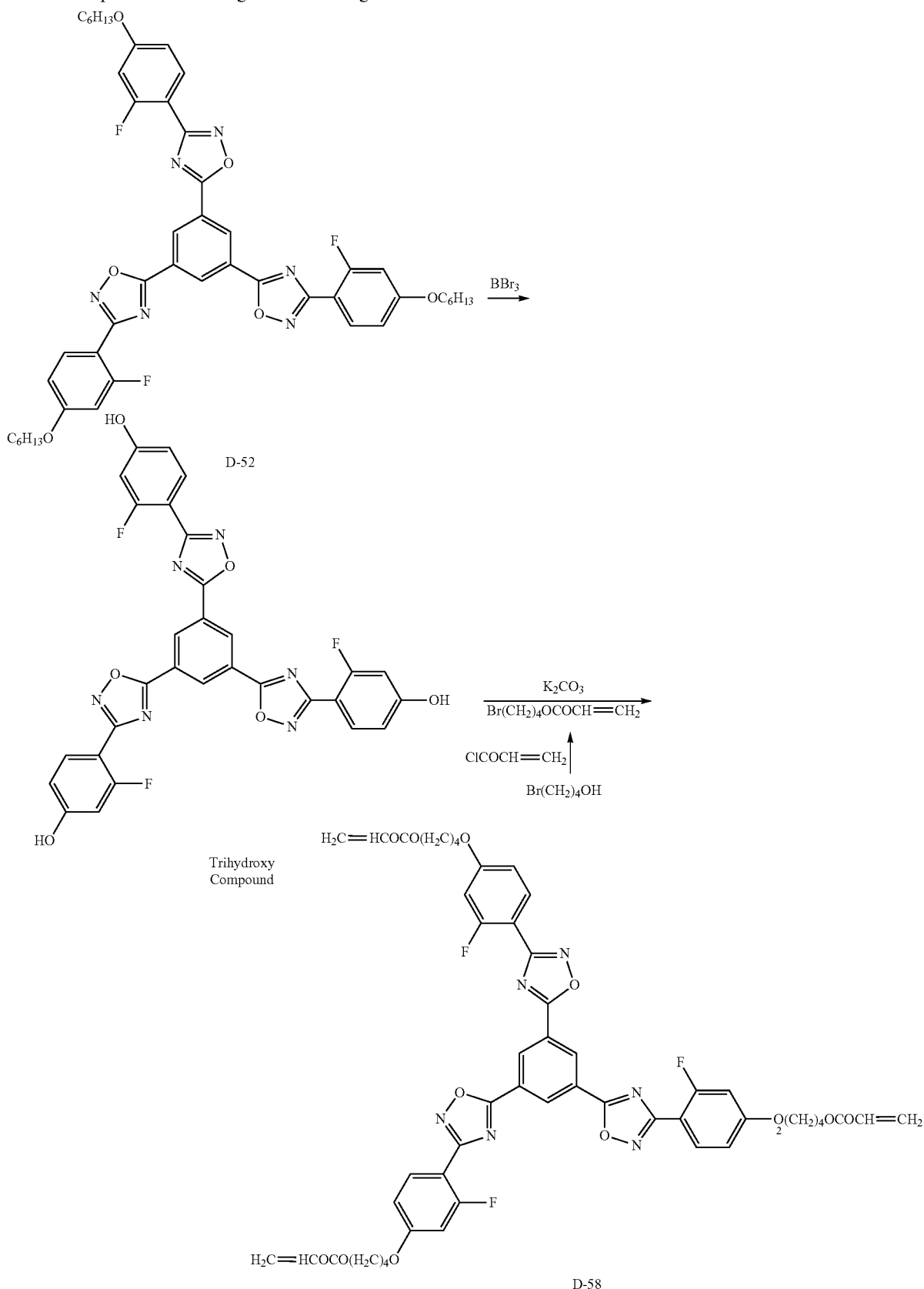

8.0 g of D-58 was obtained according to the same process as in Example 2, which, however, started from 4-bromo-1-butanol. The NMR spectrum of the thus-obtained D-58 was as follows:

$^1$H-NMR (solvent: CDCl$_3$, standard: tetramethylsilane) δ (ppm)

1.90-2.00 (12H, m)
4.10 (6H, t)
4.30 (6H, t)
5.85 (3H, dd)
6.15 (3H, dd)
6.45 (3H, dd)
6.80 (3H, dd)
6.90 (3H, dd)
8.15 (3H, t)
9.20 (3H, s)

The phase transition temperature of the thus-obtained D-58 was determined through texture observation with a polarization microscope. The temperature was elevated, and the crystal phase of the compound changed to a discotic nematic liquid-crystal phase at around 127° C. At over 139° C., the phase changed to an isotropic liquid phase. Specifically, it was found that D-58 exhibits a discotic nematic liquid-crystal phase within a temperature range of from 127° C. to 139° C.

EXAMPLE 11

[Production of D-63]

D-63 was produced according to the following scheme:

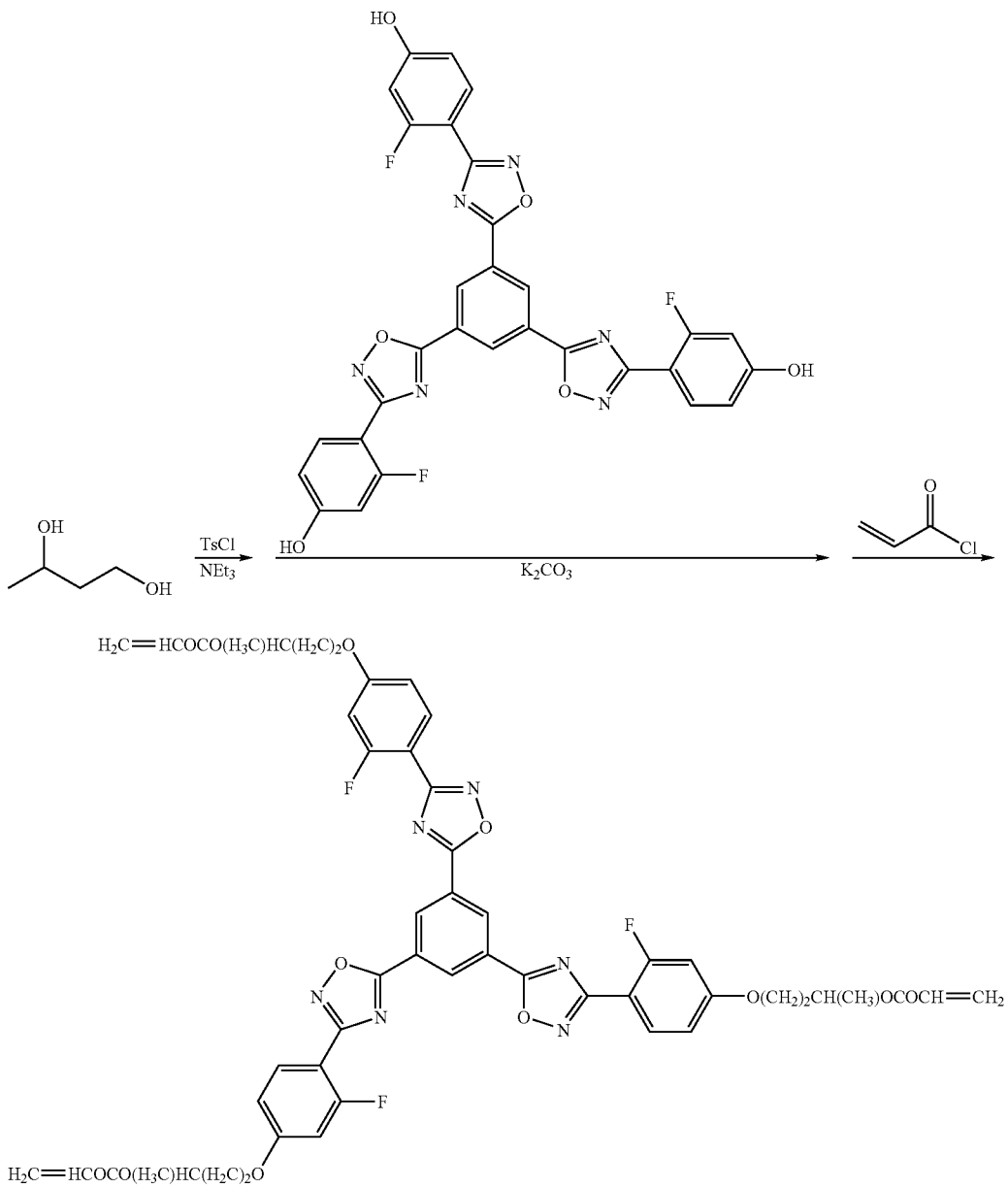

D-63

A solution prepared by dissolving 9.6 g of p-toluenesulfonyl chloride in 10 ml of acetone was dropwise added to a mixture of 9.0 ml of 1,3-butanediol and 7.7 ml of triethylamine, and this was stirred at 40° C. for 4 hours, and then 50 ml of water and 50 ml of toluene were added to it to wash the organic layer. After liquid-liquid separation, the toluene layer was evaporated away, and 3.1 g of a trihydroxy compound as above, 8.3 g of potassium carbonate, 4.5 g of sodium iodide and dimethylformamide were added to it, and stirred at 80° C. for 8 hours. Water was added to the reaction solution, and the precipitated crystal was recrystallized from tetrahydrofuran and acetonitrile. The resulting crystal was dissolved in dimethylacetamide, and 2.1 ml of acrylic acid chloride was dropwise added thereto, and stirred at 40° C. for hours. Then, 500 ml of methanol was added, and the precipitated crystal was taken out through filtration. The precipitated crystal was thus taken out through filtration, and this crystal was purified through column chromatography to obtain 1.8 g of a crystal D-68. The NMR spectrum of the thus-obtained D-68 was as follows:

$^1$H-NMR (solvent: CDCl$_3$, standard: tetramethylsilane) δ (ppm)
1.40 (9H, d)
2.15 (6H, m)
4.10 (6H, t)
5.25 (3H, m)
5.85 (3H, dd)
6.15 (3H, dd)
6.45 (3H, dd)
6.80 (3H, d)
6.85 (3H, d)
8.15 (3H, t)
9.20 (3H, s)

The phase transition temperature of the thus-obtained D-68 was determined through texture observation with a polarization microscope. The temperature was elevated, and the crystal phase of the compound changed to a discotic nematic liquid-crystal phase at around 84° C. At over 135° C., the phase changed to an isotropic liquid phase. Specifically, it was found that D-68 exhibits a discotic nematic liquid-crystal phase within a temperature range of from 84° C. to 135° C.

EXAMPLE 12

[Production of D-89]

D-89 was produced according to the following scheme:

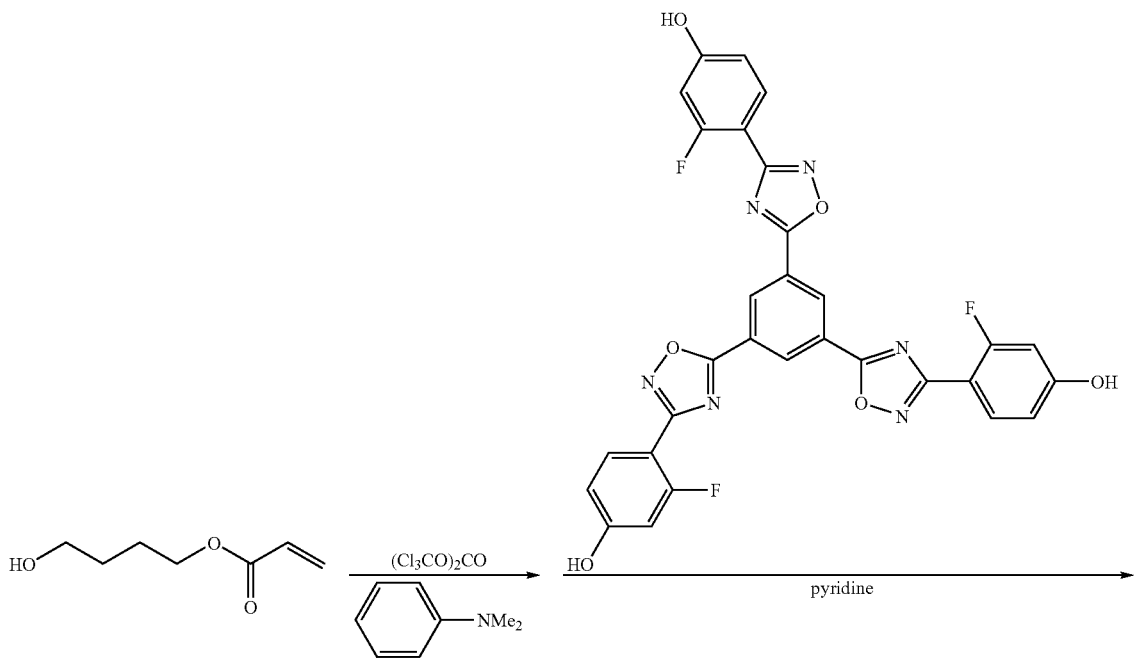

-continued

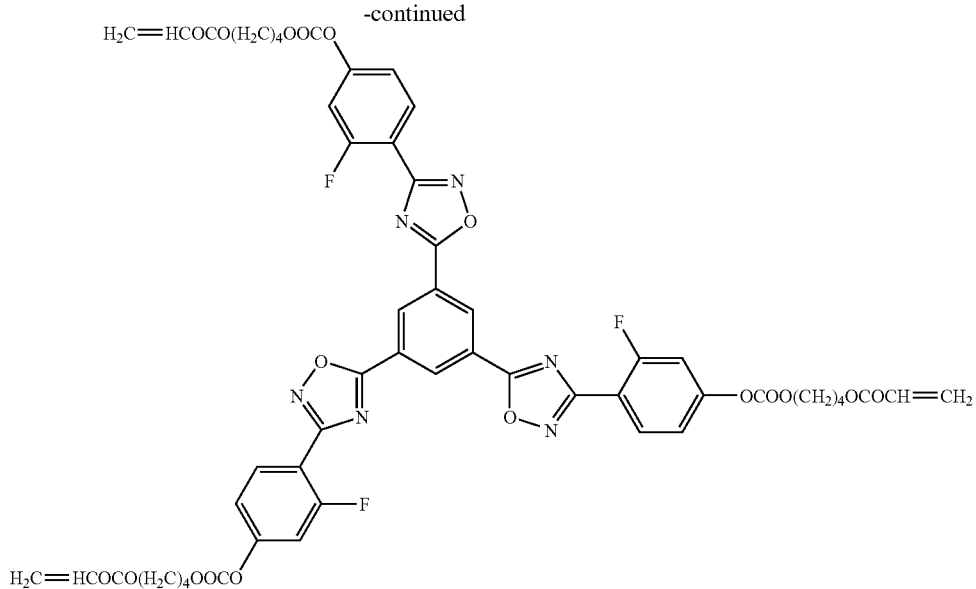

D-89

20 g of D-89 was obtained according to the same process as in Example 7, which, however, started from 4-hydroxybutyl acrylate. The NMR spectrum of the thus-obtained D-89 was as follows:

$^1$H-NMR (solvent: CDCl$_3$, standard: tetramethylsilane) δ (ppm)

1.80-2.00 (12H, m)

4.25 (6H, t)

4.35 (5H, t)

5.85 (3H, dd)

6.15 (3H, dd)

6.45 (3H, dd)

7.25 (6H, d)

8.30 (3H, t)

9.25 (3H, s)

The phase transition temperature of the thus-obtained D-89 was determined through texture observation with a polarization microscope. The temperature was elevated, and the crystal phase of the compound changed to a discotic nematic liquid-crystal phase at around 85° C. At over 104° C., the phase changed to an isotropic liquid phase. Specifically, it was found that D-89 exhibits a discotic nematic liquid-crystal phase within a temperature range of from 85° C. to 104° C.

EXAMPLE 13

[Production of D-101]

D-101 was produced according to the following scheme:

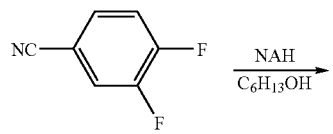

100 ml of tetrahydrofuran and 11.7 ml of hexanol were added to 5.18 g of sodium hydride. This was stirred at room temperature for 20 minutes, and then with cooling with ice, a solution prepared by dissolving 10 g of 3,4-difluorobenzonitrile in 80 ml of tetrahydrofuran was dropwise added to it. This was stirred at room temperature for 5 hours, and water was dropwise added to the reaction solution, and extracted with ethyl acetate. The organic layer was concentrated and purified through column chromatography to obtain 15.5 g of a crystal of D-101A. Next, this was processed in the same manner as in Example 1, and D-101 was thus obtained. The NMR spectrum of D-101 was as follows:

$^1$H-NMR (solvent: CDCl$_3$, standard: tetramethylsilane) δ (ppm)
0.95 (9H, t)
1.30-1.40 (12H, m)
1.40-1.50 (6H, m)
1.85-1.95 (6H, m)
4.20 (6H, t)
7.10 (3H, dd)
7.90-8.00 (6H, m)
9.20 (3H, s)

The phase transition temperature of the thus-obtained D-101 was determined through texture observation with a polarization microscope. The temperature was elevated, and the crystal phase of the compound changed to a discotic nematic liquid-crystal phase at around 135° C. At over 162° C., the phase changed to an isotropic liquid phase. Specifically, it was found that D-101 exhibits a discotic nematic liquid-crystal phase within a temperature range of from 135° C. to 162° C.

EXAMPLE 14

[Production of D-109]

D-109 was produced according to the following scheme:

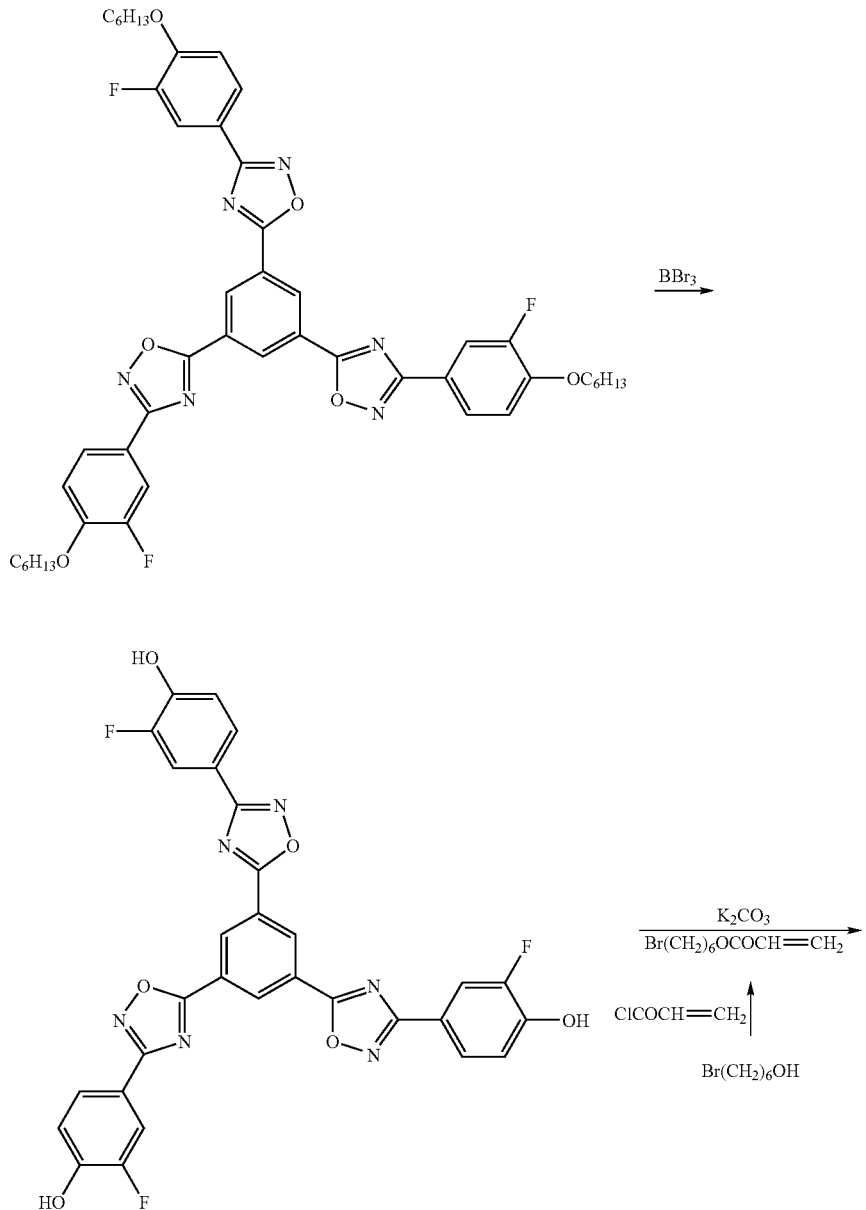

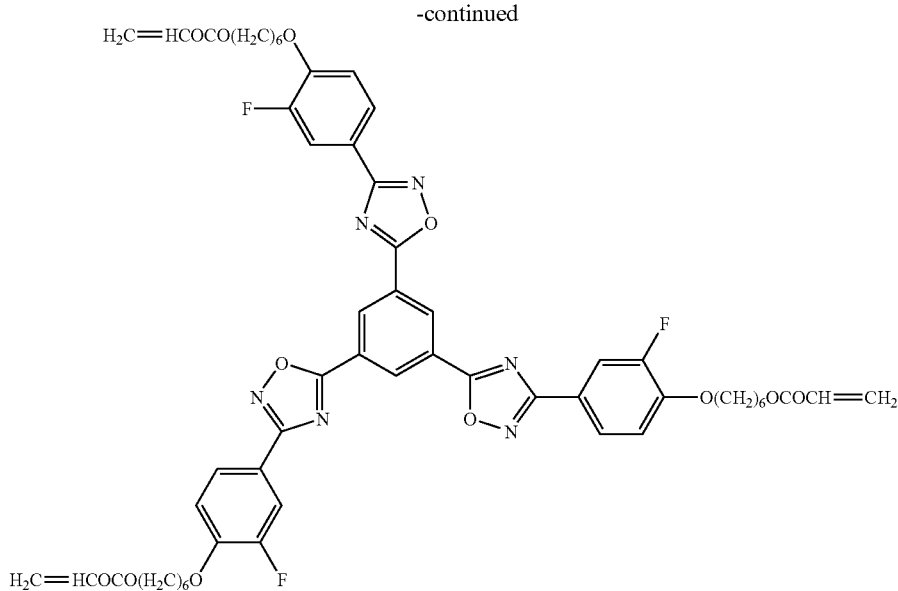

D-109

0.35 g of D-109 was obtained according to the same process as in Example 2, which, however, started from 6-bromo-1-hexanol. The NMR spectrum of the thus-obtained D-109 was as follows:

$^1$H-NMR (solvent: CDCl$_3$, standard: tetramethylsilane) δ (ppm)
1.40-1.60 (12H, m)
1.65-1.75 (6H, m)
1.75-1.85 (6H, m)
4.15 (6H, t)
4.25 (6H, t)
5.80 (3H, dd)
6.15 (3H, dd)
6.45 (3H, dd)
7.10 (3H, dd)
7.90-8.00 (6H, m)
9.25 (3H, s)

The phase transition temperature of the thus-obtained D-109 was determined through texture observation with a polarization microscope. The temperature was elevated, and the crystal phase of the compound changed to a discotic nematic liquid-crystal phase at around 79° C. At over 120° C., the phase changed to an isotropic liquid phase. Specifically, it was found that D-109 exhibits a discotic nematic liquid-crystal phase within a temperature range of from 79° C. to 120° C.

EXAMPLE 15

[Production of D-112]

D-112 was produced according to the following scheme:

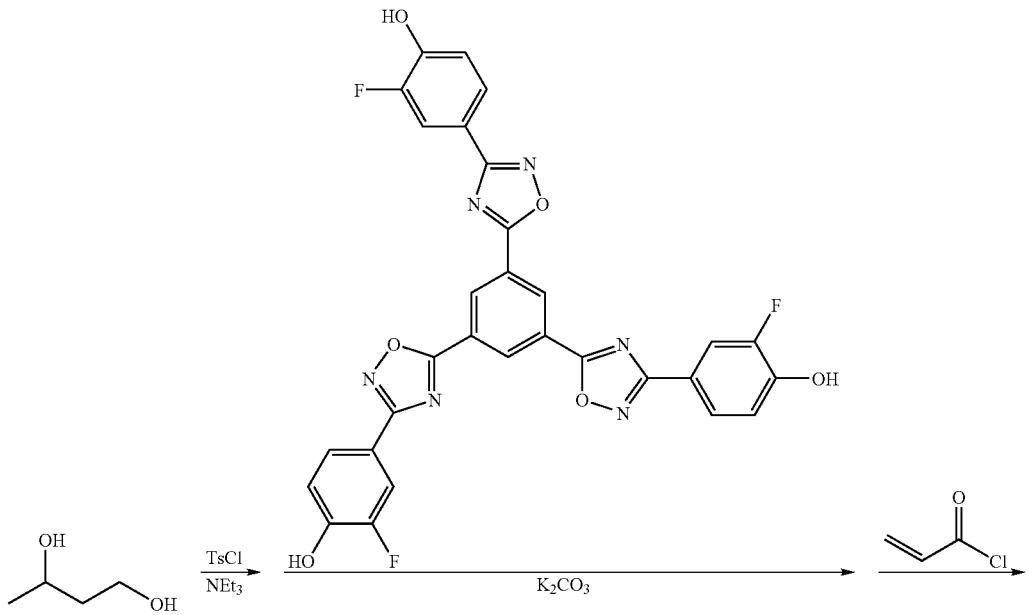

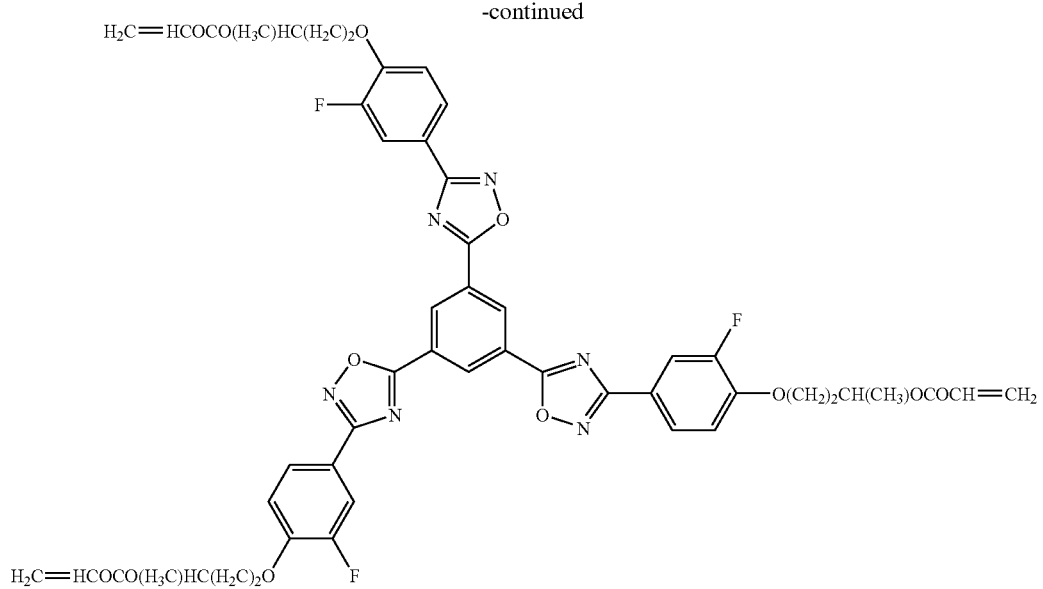

D-112

1.8 g of D-112 was obtained according to the same process as in Example 11. The NMR spectrum of the thus-obtained D-112 was as follows:

$^1$H-NMR (solvent: CDCl$_3$, standard: tetramethylsilane) δ (ppm)
1.40 (9H, d)
2.20 (6H, m)
4.20 (6H, t)
5.25 (3H, m)
5.85 (3H, dd)
6.15 (3H, dd)
6.45 (3H, dd)
7.10 (3H, t)
7.95 (6H, m)
9.20 (3H, s)

The phase transition temperature of the thus-obtained D-112 was determined through texture observation with a polarization microscope. The temperature was elevated, and the crystal phase of the compound changed to a discotic nematic liquid-crystal phase at around 124° C. At over 147° C., the phase changed to an isotropic liquid phase. Specifically, it was found that D-112 exhibits a discotic nematic liquid-crystal phase within a temperature range of from 124° C. to 147° C.

EXAMPLE 16

[Production of D-136]

D-136 was produced according to the following scheme:

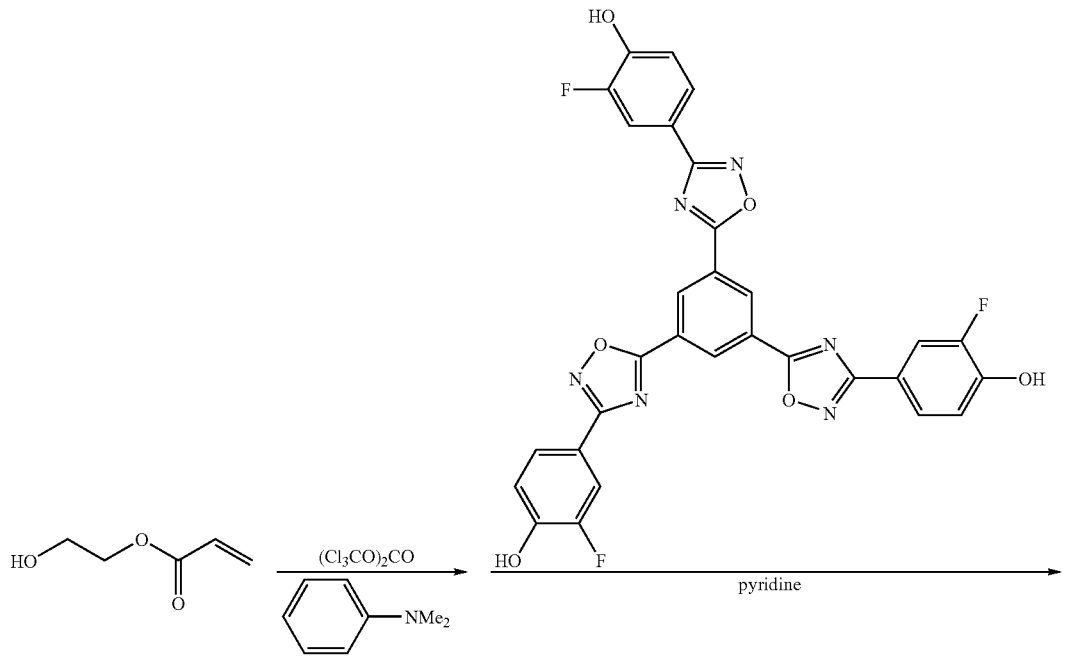

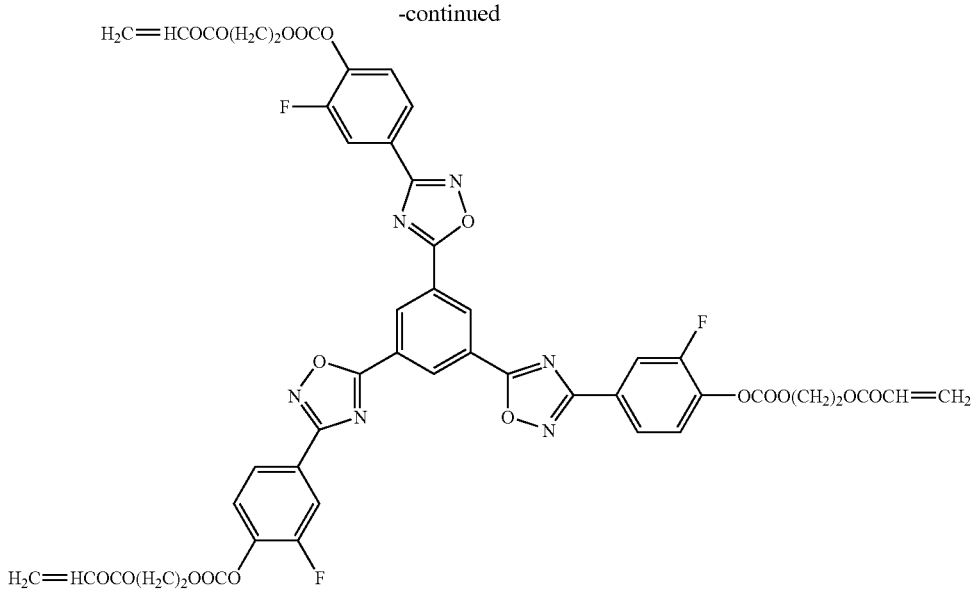

D-136

0.35 g of D-136 was obtained according to the same process as in Example 7. The NMR spectrum of the thus-obtained D-136 was as follows:

$^1$H-NMR (solvent: CDCl$_3$, standard: tetramethylsilane) δ (ppm)
4.50 (6H, t)
4.60 (6H, t)
5.92 (3H, dd)
6.20 (3H, dd)
6.50 (3H, dd)
7.45 (31-1, dd)
8.10-8.20 (6H, m)
9.30 (3H, s)

The phase transition temperature of the thus-obtained D-136 was determined through texture observation with a polarization microscope. The temperature was elevated, and the crystal phase of the compound changed to a discotic nematic liquid-crystal phase at around 128° C. At over 129° C., the phase changed to an isotropic liquid phase. Specifically, it was found that D-136 exhibits a discotic nematic liquid-crystal phase within a temperature range of from 128° C. to 129° C.

EXAMPLE 17

[Production of D-148]

D-148 was produced according to the following scheme:

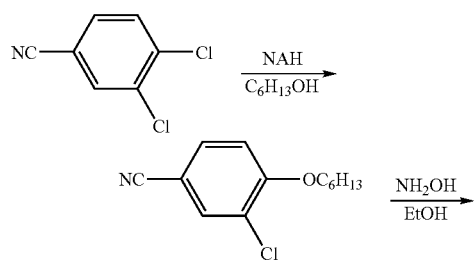

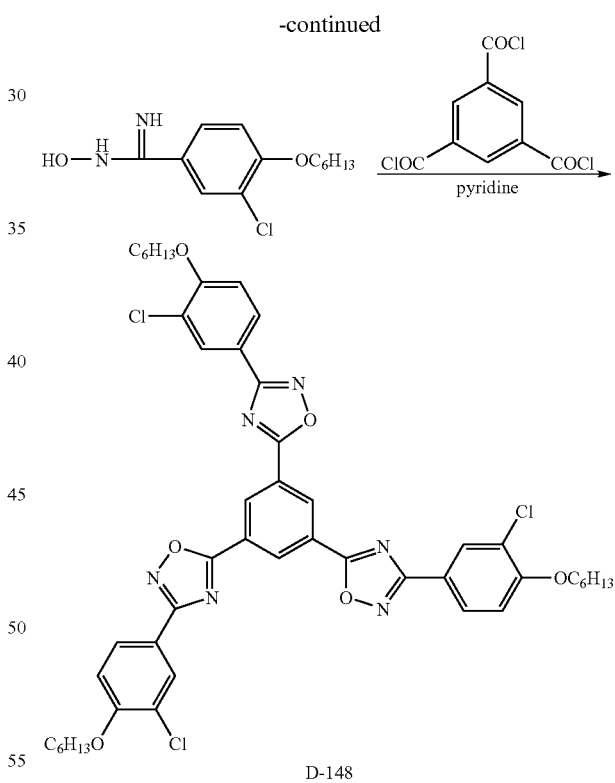

D-148

2.5 g of D-148 was obtained according to the same process as in Example 12. The NMR spectrum of the thus-obtained D-148 was as follows:

$^1$H-NMR (solvent: CDCl$_3$, standard: tetramethylsilane) δ (ppm)
0.90 (9H, t)
1.30-1.40 (12H, m)
1.40-1.50 (6H, m)
1.85-1.95 (6H, m)
4.10 (6H, t)

7.02 (3H, d)

8.10 (3H, dd)

8.25 (3H, d)

9.20 (3H, s)

The phase transition temperature of the thus-obtained D-148 was determined through texture observation with a polarization microscope. The temperature was elevated, and the crystal phase of the compound changed to a discotic nematic liquid-crystal phase at around 145° C. At over 167° C., the phase changed to an isotropic liquid phase. Specifically, it was found that D-148 exhibits a discotic nematic liquid-crystal phase within a temperature range of from 145° C. to 167° C.

EXAMPLE 18

[Production of D-157]

D-157 was produced according to the following scheme:

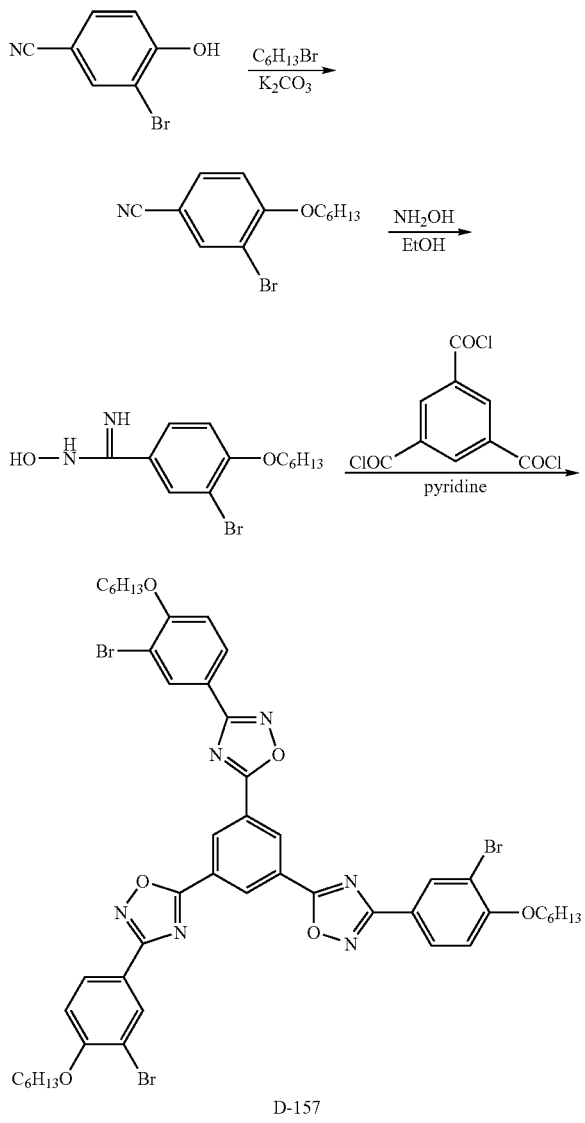

6.5 g of D-157 was obtained according to the same process as in Example 1, for which, however, the starting compound was changed as in the above. The NMR spectrum of the thus-obtained D-157 was as follows:

$^1$H-NMR (solvent: CDCl$_3$, standard: tetramethylsilane) δ (ppm)

0.90 (9H, t)

1.30-1.40 (12H, m)

1.40-1.50 (6H, m)

1.85-1.95 (6H, m)

4.10 (6H, t)

7.00 (3H, d)

8.10 (3H, dd)

8.40 (3H, d)

9.20 (3H, s)

The phase transition temperature of the thus-obtained D-157 was determined through texture observation with a polarization microscope. The temperature was elevated, and the crystal phase of the compound changed to a liquid-crystal phase at around 166° C. At over 168° C., the phase changed to an isotropic liquid phase. Next, when the compound was gradually cooled from 170° C., then its phase changed to a discotic nematic phase at around 157° C. Further cooled to 140° C., its phase again changed to a crystal phase. Specifically, it was found that, while heated, D-157 exhibits a columnar phase within a temperature range of from 166° C. to 168° C., and while cooled, it exhibits a discotic nematic phase within a temperature range of from 157° C. to 140° C.

EXAMPLE 19

[Production of D-166]

D-166 was produced according to the following scheme:

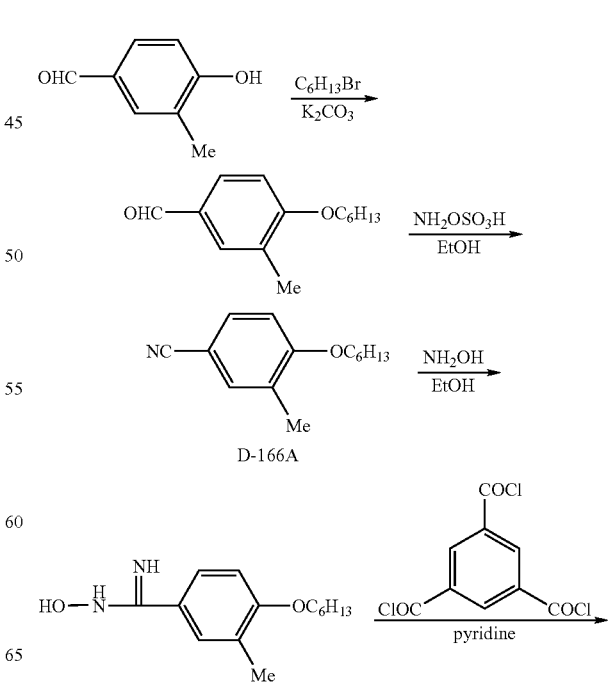

-continued

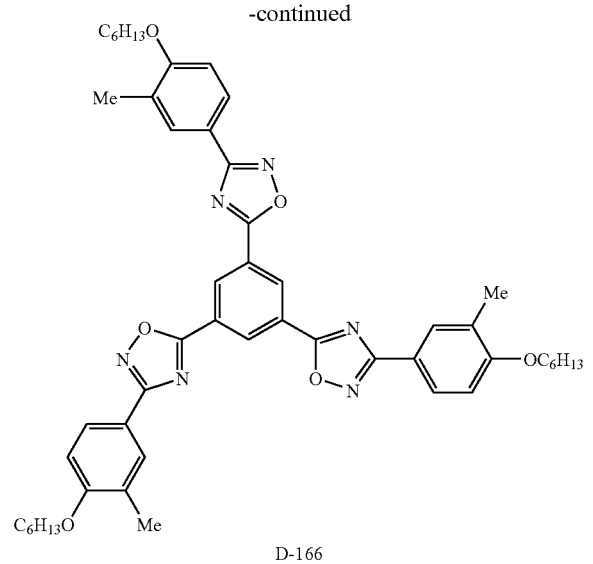

D-166

5.5 g of 3-methyl-4-hydroxybenzaldehyde was dissolved in 50 ml of dimethylformamide, to which were added 8.4 g of potassium carbonate and 6.8 g of 1-bromohexane. Then, this was stirred under nitrogen atmosphere at 110° C. for 5 hours. Water was added to the reaction solution, extracted with ethyl acetate, and washed with saturated saline. The organic layer was concentrated under reduced pressure, and 100 ml of ethanol was added to the resulting oily product. With cooling with ice, an aqueous solution of 9.0 g of hydroxylamine-O-sulfonic acid was dropwise added to it. This was reacted at 55° C. for 6 hours, and water was added to the reaction solution, extracted with ethyl acetate and washed with saturated saline. The organic layer was concentrated under reduced pressure and purified through column chromatography to obtain 5.6 g of D-166A.

Next, D-166A was converted into D-166 in the same manner as in Example 1. The yield of D-166 was 3.0 g. The NMR spectrum of the thus-obtained D-166 was as follows:

$^1$H-NMR (solvent: CDCl$_3$, standard: tetramethylsilane) δ (ppm)
0.90 (9H, t)
1.30-1.40 (12H, m)
1.50-1.60 (6H, m)
1.80-1.90 (6H, m)
2.32 (9H, s)
4.05 (6H, t)
6.92 (3H, d)
8.00 (3H, d)
8.02 (3H, dd)
9.20 (3H, s)

The phase transition temperature of the thus-obtained D-166 was determined through texture observation with a polarization microscope. The temperature was elevated, and the crystal phase of the compound changed to a discotic nematic liquid-crystal phase at around 135° C. At over 160° C., the phase changed to an isotropic liquid phase. Specifically, it was found that D-166 exhibits a discotic nematic liquid-crystal phase within a temperature range of from 135° C. to 160° C.

EXAMPLE 20

[Production of D-175]

D-175 was produced according to the following scheme:

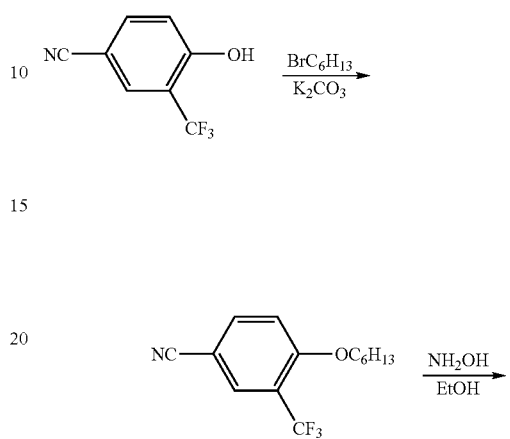

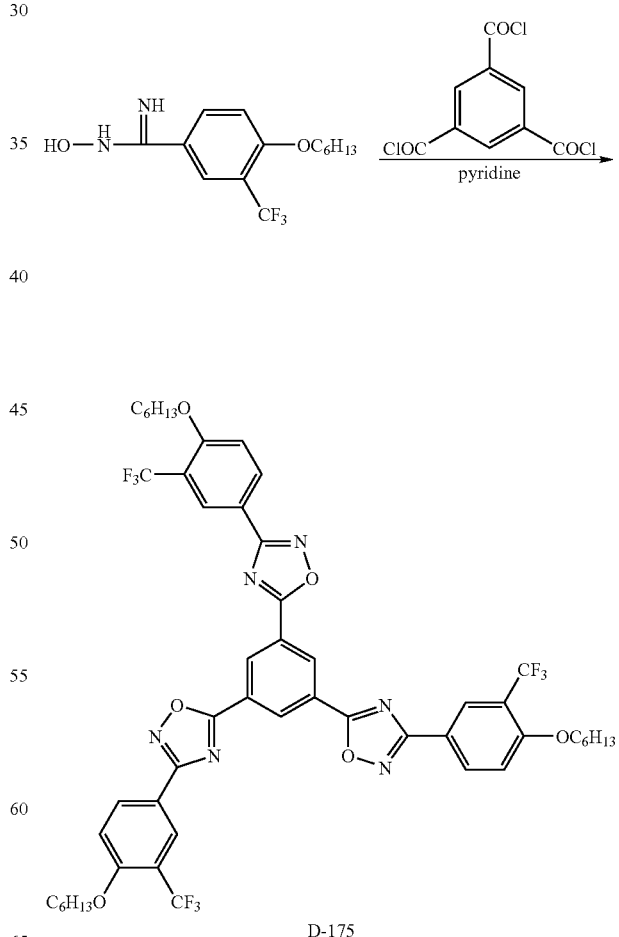

D-175

5.2 g of D-175 was obtained according to the same process as in Example 1, for which, however, the starting compound was changed as in the above. The NMR spectrum of the thus-obtained D-175 was as follows:

$^1$H-NMR (solvent: CDCl$_3$, standard: tetramethylsilane) δ (ppm)

0.90 (9H, t)

1.30-1.40 (12H, m)

1.50-1.60 (6H, m)

1.80-1.90 (6H, m)

4.15 (6H, t)

7.15 (3H, d)

8.35 (3H, dd)

8.45 (3H, d)

9.25 (3H, s)

The phase transition temperature of the thus-obtained D-175 was determined through texture observation with a polarization microscope. First, the temperature was elevated, and the crystal phase of the compound changed to an isotropic liquid phase at around 131° C. Next, the temperature was gradually lowered from 131° C., and the phase of the compound changed to a discotic nematic phase at around 124° C. At around 106° C., the discotic nematic phase of the compound changed to a columnar phase. Further cooled to 88° C., the phase of the compound again changed to a crystal phase. Specifically, it was found that D-175 exhibits a discotic nematic phase within a temperature range of from 124° C. to 106° C.

EXAMPLE 21

[Production of D-194]

D-194 was produced according to the following scheme:

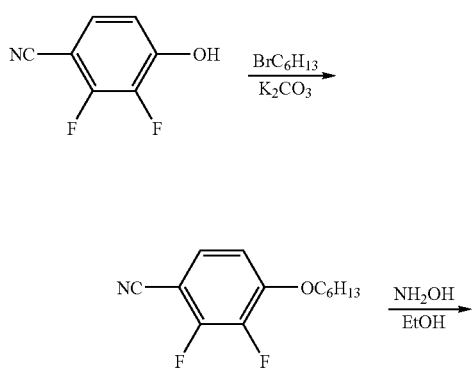

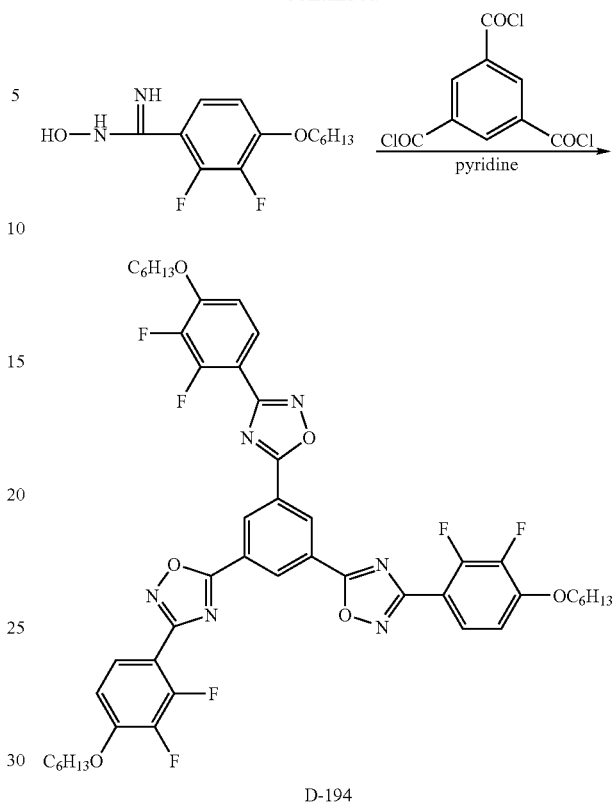

D-194

1.0 g of D-194 was obtained according to the same process as in Example 1, for which, however, the starting compound was changed as in the above. The NMR spectrum of the thus-obtained D-194 was as follows:

$^1$H-NMR (solvent: CDCl$_3$, standard: tetramethylsilane) δ (ppm)

0.95 (9H, t)

1.30-1.40 (12H, m)

1.50-1.60 (6H, m)

1.85-1.95 (6H, m)

4.15 (6H, t)

6.85-6.95 (3H, m)

7.90-8.00 (3H, m)

9.25 (3H, s)

The phase transition temperature of the thus-obtained D-194 was determined through texture observation with a polarization microscope. The ambient temperature was elevated, and the crystal phase of the compound changed to a discotic nematic liquid-crystal phase at around 119° C. At over 149° C., the phase changed to an isotropic liquid phase. Specifically, it was found that D-194 exhibits a discotic nematic liquid-crystal phase within a temperature range of from 119° C. to 149° C.

EXAMPLE 22

[Production of D-201]

D-201 was produced according to the following scheme:

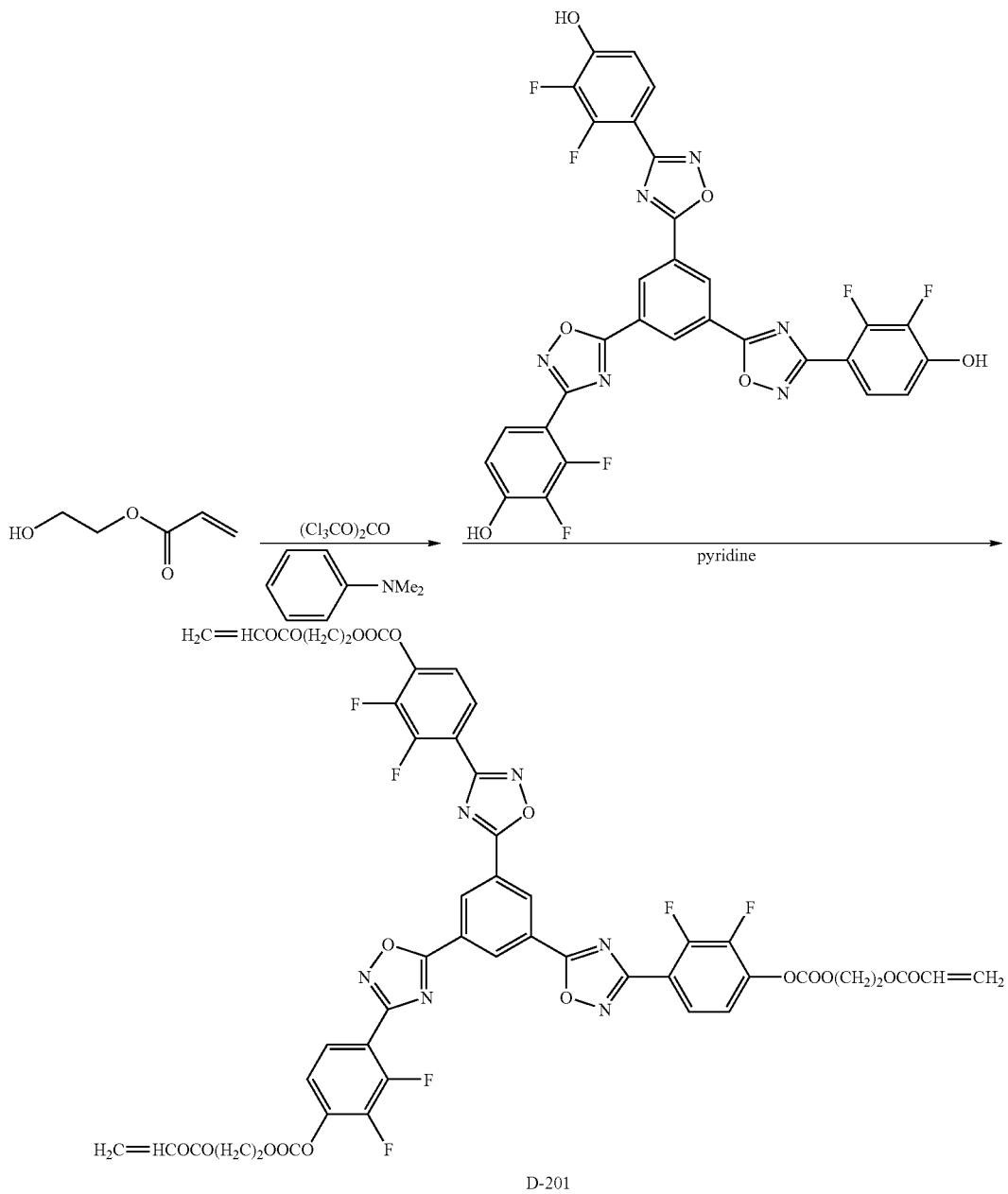

D-201

A trihydroxy compound was produced in the same manner as in Example 2, for which, however, the starting compound was changed as in the above. Using this, 0.35 g of D-201 was obtained in the same manner as in Example 7. The NMR spectrum of the thus-obtained D-201 was as follows:

$^1$H-NMR (solvent: CDCl$_3$, standard: tetramethylsilane) δ (ppm)
4.50 (6H, t)
4.60 (6H, t)
5.90 (3H, dd)
6.20 (3H, dd)
6.50 (3H, dd)
7.20-7.30 (3H, m)
8.00-8.10 (3H, m)
9.30 (3H, s)

The phase transition temperature of the thus-obtained D-201 was determined through texture observation with a polarization microscope. The ambient temperature was elevated, and the crystal phase of the compound changed to a discotic nematic liquid-crystal phase at around 75° C. At over 117° C., the phase changed to an isotropic liquid phase. Specifically, it was found that D-201 exhibits a discotic nematic liquid-crystal phase within a temperature range of from 75° C. to 117° C.

EXAMPLE 23

[Production of D-250]

D-250 was produced according to the following scheme:

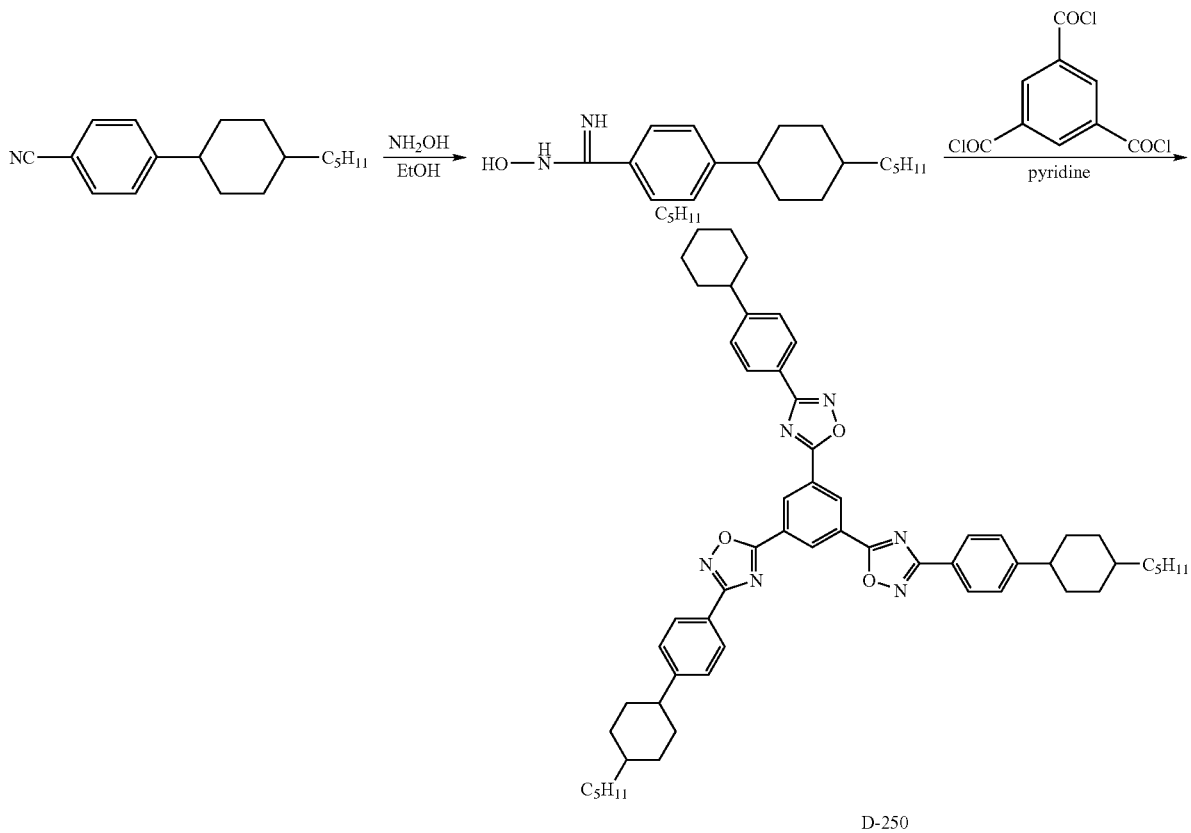

0.3 g of D-250 was obtained according to the same process as in Example 1. The NMR spectrum of the thus-obtained D-250 was as follows:

$^1$H-NMR (solvent: CDCl$_3$, standard: tetramethylsilane) δ (ppm)
0.90 (9H, t)
1.00-1.10 (6H, m)
1.20-1.40 (24H, m)
1.50-1.60 (6H, m)
1.90-2.00 (12H, m)
7.40 (6H, d)
8.15 (6H, d)
9.23 (3H, s)

The phase transition temperature of the thus-obtained D-250 was determined through texture observation with a polarization microscope. The ambient temperature was elevated, and the crystal phase of the compound changed to an isotropic liquid phase at around 232° C. Then, the temperature was gradually lowered from 232° C., and the phase of the compound changed to a discotic nematic phase at around 199° C. Further lowered to 169° C., the phase again changed to a crystal phase. Specifically, it was found that, while cooled, D-250 exhibits a discotic nematic phase within a temperature range of from 199° C. to 169° C.

EXAMPLE 24

[Production of D-298]

D-298 was produced according to the following scheme:

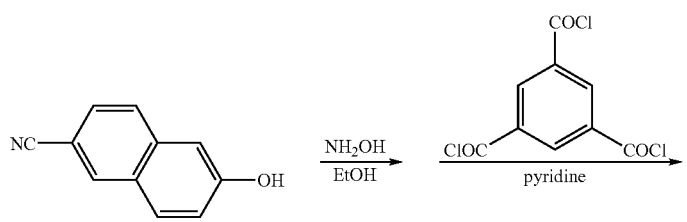

-continued

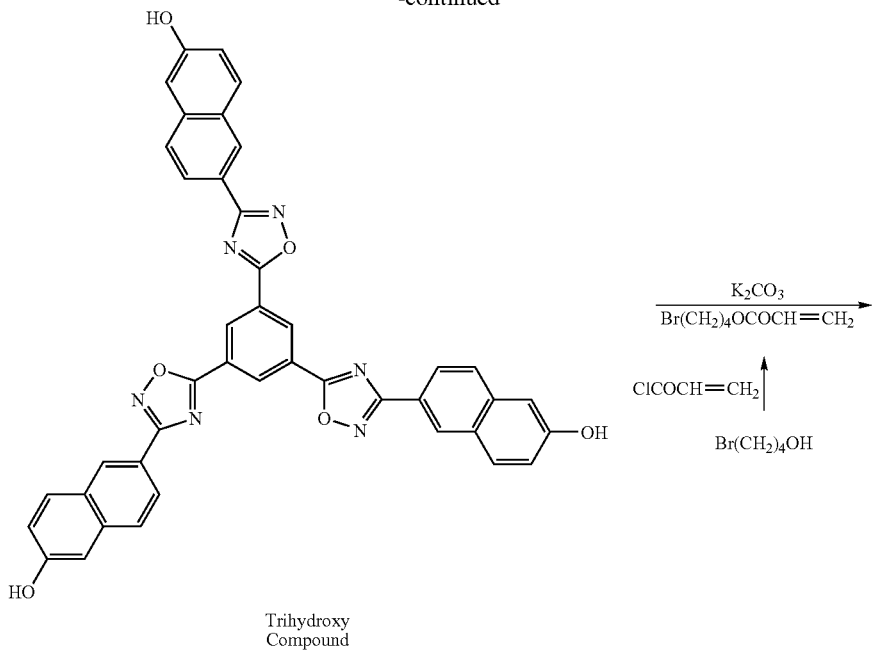

Trihydroxy Compound

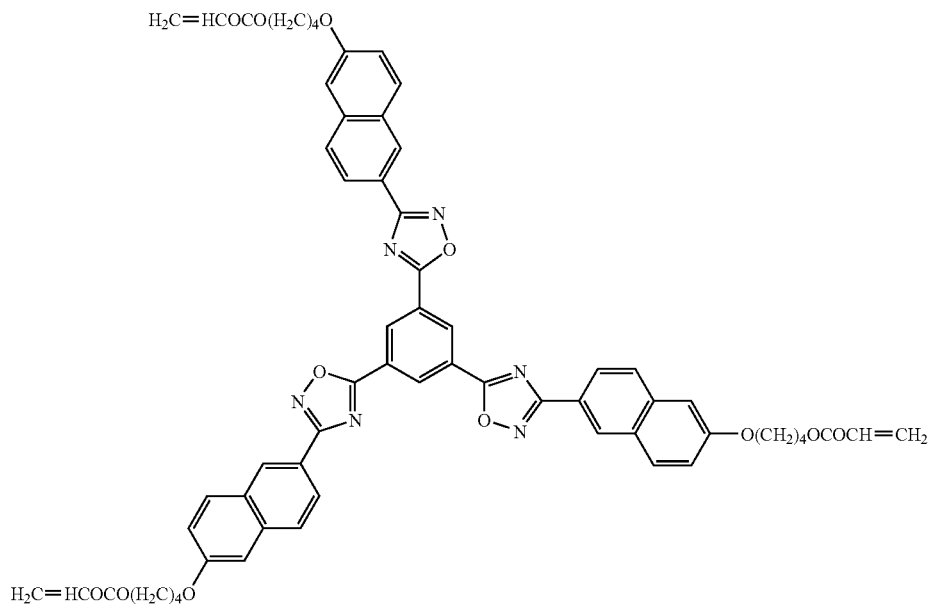

D-298

21 g of 6-cyano-2-naphthol was dissolved in 210 ml of methanol, and 66 ml of an aqueous solution of 50% hydroxylamine was dropwise added thereto. This was stirred at 40° C. for 5 hours, and water with ice was added to the reaction solution. The precipitated crystal was taken out through filtration. The crystal was dissolved in 250 ml of dimethylacetamide, and 11 ml of pyridine was added thereto. A solution prepared by dissolving 9.8 g of trimesic acid chloride in 25 ml of acetonitrile was dropwise added to it, stirred at 100° C. for 2 hours. Then, water with ice was added to the reaction solution, and the precipitated crystal was taken out through filtration. The crystal was dried, and 20 g of a trihydroxy compound as above was obtained.

Next, using 4-bromo-1-butanol as the starting compound, 0.53 g of D-298 was obtained in the same manner as in Example 2. The NMR spectrum of the thus-obtained D-298 was as follows:

$^1$H-NMR (solvent: CDCl$_3$, standard: tetramethylsilane) δ (ppm)
1.90-2.05 (12H, m)
4.15 (6H, t)
4.20 (6H, t)
5.85 (3H, dd)
6.15 (3H, dd)
6.45 (3H, dd)
7.15-7.30 (6H, m)

7.85 (3H, d)
7.95 (3H, d)
8.25 (3H, d)
8.70 (3H, s)
9.30 (3H, s)

The phase transition temperature of the thus-obtained D-298 was determined through texture observation with a polarization microscope. The ambient temperature was elevated, and the crystal phase of the compound changed to a nematic liquid-crystal phase at around 166° C. At over 215° C., the phase changed to an isotropic liquid phase. Specifically, it was found that D-298 exhibits a nematic liquid-crystal phase within a temperature range of from 166° C. to 215° C.

EXAMPLE 25

[Production of D-303]

D-303 was produced according to the following scheme:

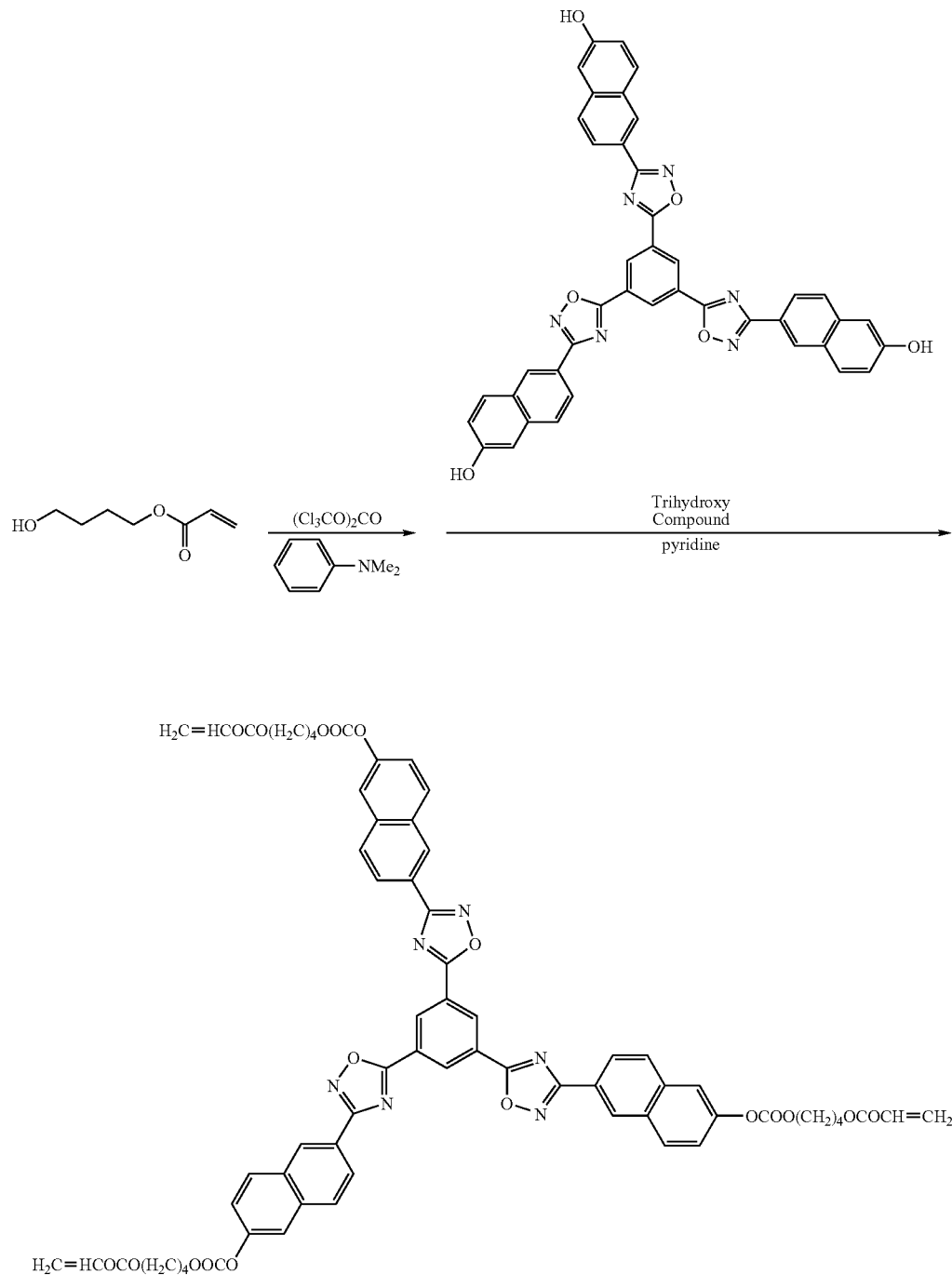

D-303

0.78 g of D-303 was obtained according to the same process as in Example 7, which, however, started from 4-hydroxybutyl acrylate. The NMR spectrum of the thus-obtained D-303 was as follows:

$^1$H-NMR (solvent: CDCl$_3$, standard: tetramethylsilane) δ (ppm)
1.85-2.00 (12H, m)
4.25 (6H, m)
4.35 (6H, m)
5.85 (6H, d)
6.15 (3H, dd)
6.45 (3H, d)
7.45 (3H, d)
7.70 (3H, s)
7.95 (3H, d)
8.05 (3H, d)
8.30 (3H, d)
8.80 (3H, s)
9.30 (3H, s)

The phase transition temperature of the thus-obtained D-303 was determined through texture observation with a polarization microscope: The ambient temperature was elevated, and the crystal phase of the compound changed to a discotic nematic liquid-crystal phase at around 170° C. At over 220° C., the phase changed to an isotropic liquid phase. Specifically, it was found that D-303 exhibits a discotic nematic liquid-crystal phase within a temperature range of from 170° C. to 220° C.

EXAMPLE 26

[Production of D-304]

0.60 g of D-304 was obtained according to the same process as in Example 7, which, however, started from 2-(2-hydroxyethyl)ethyl acrylate. The NMR spectrum of the thus-obtained D-304 was as follows:

$^1$H-NMR (solvent: CDCl$_3$, standard: tetramethylsilane) δ (ppm)
3.80-3.90 (12H, m)
4.35 (6H, t)
4.45 (6H, t)
5.85 (3H, dd)
6.20 (3H, dd)
6.45 (3H, dd)
7.45 (3H, d)
7.70 (3H, s)
7.95 (3H, d)
8.05 (3H, d)
8.25 (3H, d)
8.75 (3H, s)
9.30 (3H, s)

The phase transition temperature of the thus-obtained D-304 was determined through texture observation with a polarization microscope. The ambient temperature was elevated, and the crystal phase of the compound changed to a columnar liquid-crystal phase at around 108° C. Further heated, the columnar phase changed to a discotic nematic liquid-crystal phase at around 111° C. At over 197° C., the phase changed to an isotropic liquid phase. Specifically, it was found that D-304 exhibits a discotic nematic liquid-crystal phase within a temperature range of from 111° C. to 197° C.

EXAMPLE 27

[Fabrication of Thin Film of Uniformly-Aligned D-89]

An aqueous solution of PVA-203 (by Kuraray) was applied onto a glass substrate, and dried at 100° C. for 3 minutes. The thickness of PVA-203 was 0.5 μm. A coating solution mentioned below was applied onto the substrate coated with the thin film of PVA-203 in a mode of spin coating, and put into a thermostat tank at 90° C. After 5 minutes, 600 mJ UV rays were applied to it, and the alignment of the liquid-crystalline film was thereby fixed. After left cooled to room temperature, the alignment of the film was observed with a polarization microscope, which confirmed that the discotic liquid-crystalline compound was homeotropically aligned with no defect. The thickness of the liquid-crystalline compound layer was 3.3 μm.

| (Coating Solution) | |
|---|---|
| Liquid-Crystalline Compound D-89 | 100 mas. pts. |
| Air-Interface Alignment-Controlling Agent V-(1) | 0.2 mas. pts. |
| Irgacure 907 (by Nagase Sangyo) | 3.0 mas. pts. |
| Diethylthioxanthone | 1.0 mas. pts. |
| Methyl Ethyl Ketone | 250 mas. pts. |

Air-Interface Alignment-Controlling Agent V-(1):

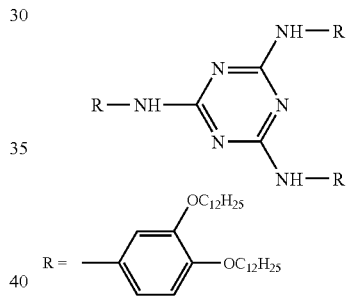

EXAMPLE 28

[Fabrication of Thin Film of Uniformly-Aligned D-109]

A coating solution mentioned below was applied onto the substrate coated with the thin film of PVA-203 in a mode of spin coating, and put into a thermostat tank at 100° C. After 5 minutes, 600 mJ UV rays were applied to it, and the alignment of the liquid-crystalline film was thereby fixed. After left cooled to room temperature, the alignment of the film was observed with a polarization microscope, which confirmed that the discotic liquid-crystalline compound was homeotropically aligned with no defect. The thickness of the liquid-crystalline compound layer was 3.0 μm.

| (Coating Solution) | |
|---|---|
| Liquid-Crystalline Compound D-109 | 100 mas. pts. |
| Air-Interface Alignment-Controlling Agent V-(1) | 0.2 mas. pts. |
| Irgacure 907 (by Nagase Sangyo) | 3.0 mas. pts. |
| Diethylthioxanthone | 1.0 mas. pts. |
| Methyl Ethyl Ketone | 250 mas. pts. |

COMPARATIVE EXAMPLE 1

[Fabrication of Thin Film of Uniformly-Aligned, Conventional Discotic Liquid-Crystalline Compound]

A coating solution mentioned below was applied onto the substrate coated with the thin film of PVA-203 in a mode of spin coating, and put into a thermostat tank at 190° C. After 5 minutes, 600 mJ UV rays were applied to it, and the alignment of the liquid-crystalline film was thereby fixed. After left cooled to room temperature, the alignment of the film was observed with a polarization microscope, which confirmed that the discotic liquid-crystalline compound was homeotropically aligned with no defect. The thickness of the liquid-crystalline compound layer was 3.0 μm.

(Coating Solution)

| | |
|---|---|
| Liquid-Crystalline Compound JD-1 mentioned below | 100 mas. pts. |
| Air-Interface Alignment-Controlling Agent V-(1) | 0.2 mas. pts. |
| Irgacure 907 (by Nagase Sangyo) | 3.0 mas. pts. |
| Diethylthioxanthone | 1.0 mas. pt. |
| Methyl Ethyl Ketone | 250 mas. pts. |

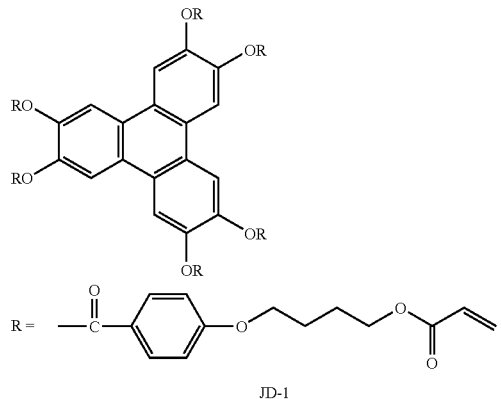

JD-1

[Comparison in Point of Δn and Wavelength Dispersiveness]

The wavelength dispersion value (Re (478 nm)/Re (748 nm)) of the thin film obtained in Examples 27 and 28 and Comparative Example 1 was determined by the use of KOBRA (by Oji Keisokuki), derived from the retardation thereof measured at 478 nm and 748 nm at an oblique angle of 40°.

Also using KOBRA (by Oji Keisokuki), Δn of the thin film was determined as follows: At a wavelength of 589 nm, the retardation of the thin film was measured at different angles. On the supposition that the film is an index ellipsoid model, Δn·d of the film was computed according to the method described in Designing Concepts of the Discotic Negative Compensation Films SID98 DIGEST. This was divided by the film thickness (d) separately measured, and Δn was thus obtained. The results are given in Table 1.

TABLE 1

| | | Δn | Wavelength Dispersion Value |
|---|---|---|---|
| Example 27 | Liquid-Crystalline Compound D-89 of the Invention | 0.11 | 1.10 |
| Example 28 | Liquid-Crystalline Compound D-109 of the Invention | 0.14 | 1.12 |

TABLE 1-continued

| | | Δn | Wavelength Dispersion Value |
|---|---|---|---|
| Comparative Example 1 | Conventional Liquid-Crystalline Compound JD-1 | 0.09 | 1.18 |

The results in Table 1 confirm that the liquid-crystalline compounds of the invention have the advantages of higher Δn and lower wavelength dispersiveness as compared with the conventional liquid-crystalline compound.

COMPARATIVE EXAMPLE 2

The following compound JD-2, which had been produced according to a method described in a reference (Kim, Bong Gi et al's report, Molecular Crystals and Liquid Crystals, 2001, Vol. 370, p. 391), was injected into a horizontal alignment cell (EHC's KSRP-10/A107M1NSS (ZZ)) with a cell gap of 10 μm, at 150° C., and homeotropically aligned therein at 130° C. Next, its wavelength dispersion value was determined according to the method mentioned above, and it was 1.19.

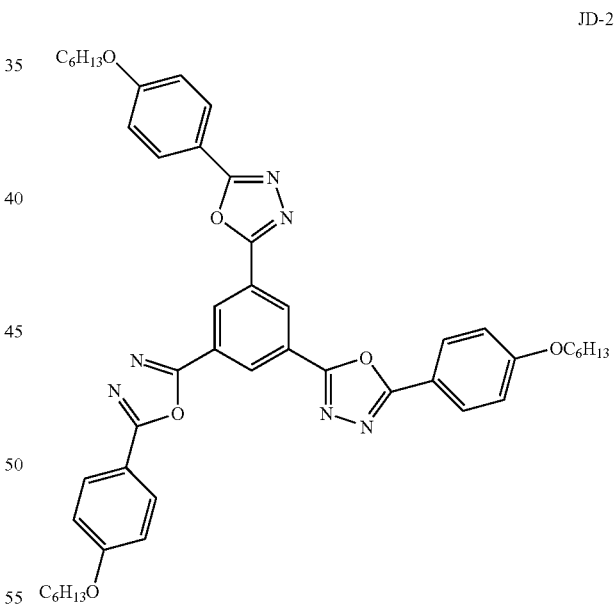

JD-2

COMPARATIVE EXAMPLE 3

The following liquid-crystalline compound JD-3 was injected into a horizontal alignment cell (EHC's KSRP-10/A1071M1NSS (ZZ)) with a cell gap of 10 μm, at 200° C., and homeotropically aligned therein at 190° C. Next, its wavelength dispersion value was determined according to the method mentioned above, and it was 1.18.

JD-3

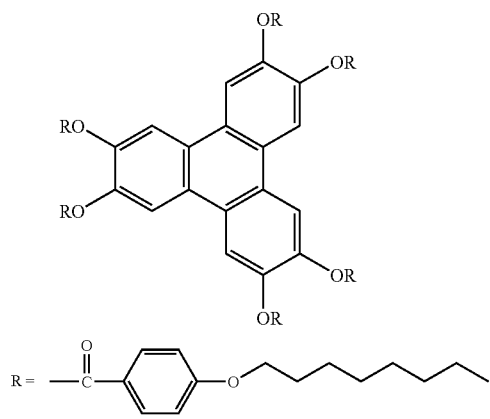

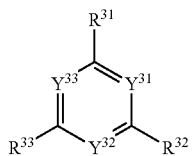

The results of Comparative Example 2 and Comparative Example 3 confirm that the liquid-crystalline compounds of the invention have the advantage of lower wavelength dispersiveness than that of not only the conventional, non-polymerization-type liquid-crystalline compound JD-3 but also the conventional liquid-crystalline compound JD-2 having a similar skeleton to that of the compound of the invention.

The invention claimed is:

1. A compound represented by the following formula (DII):

(DII)

$$\begin{array}{c} R^{31} \\ Y^{33} \diagup Y^{31} \\ R^{33} \diagdown Y^{32} \diagdown R^{32} \end{array}$$

wherein $Y^{31}$, $Y^{32}$ and $Y^{33}$ each represents a methine group; $R^{31}$, $R^{32}$ and $R^{33}$ each independently represents the following formula (DII-R):

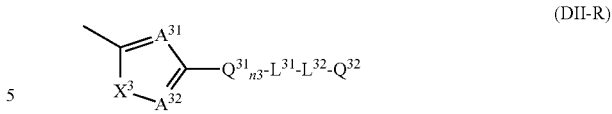

(DII-R)

wherein $A^{31}$ and $A^{32}$ each independently represent a methine group or a nitrogen atom; $X^3$ represents an oxygen atom, a sulfur atom, a methylene group or an imino group; $Q^{31}$ represents a naphthalene group; n3 indicates an integer of from 1 to 3;

$L^{31}$ represents *—O—, *—O—CO—, *—CO—O—, *—O—CO—O—, *—S—, *—NH—, *—SO$_2$—, *—CH$_2$—, *—CH=CH— or *—C≡C—; * indicates the position at which the group bonds to $Q^{31}$; $L^{32}$ represents a divalent linking group selected from the group consisting of —O—, —S—, —C(=O)—, —SO$_2$—, —NH—, —CH$_2$—, —CH=CH— and —C≡C— and a combination thereof, and when the divalent linking group contains a hydrogen atom, then the hydrogen atom may be substituted with a substituent; $Q^{32}$ represents a polymerizable group or a hydrogen atom, and when the polymerizable group contains a hydrogen atom, then the hydrogen atom may be substituted with a substituent.

2. The compound of claim 1, wherein in formula (DII-R), $A^{31}$ and $A^{32}$ are both nitrogen atoms, and $X^3$ is an oxygen atom.

3. The compound of claim 1, which is a liquid-crystalline compound.

4. A composition containing at least one compound of claim 3.

5. A thin film comprising the compound of claim 3, wherein the compound is uniformly aligned.

6. The thin film of claim 5, wherein the alignment is fixed.

7. The compound of claim 1, wherein in formula (DII-R), $L^{31}$ is —O—, —O—CO—, —O—CO—O— or —CH$_2$— in which ** indicates the position at which the group bonds to $Q^{31}$.

8. The compound of claim 1, wherein in formula (DII-R), $L^{32}$ is —O—, —C(=O)—, —CH$_2$—, —CH=CH—, —C≡C— or a combination thereof.

9. The compound of claim 1, wherein in formula (DII-R), $Q^{32}$ is a polymerizable group.

* * * * *